(12) United States Patent
Nakamura et al.

(10) Patent No.: US 8,901,302 B2
(45) Date of Patent: Dec. 2, 2014

(54) PYRAZINO[2,3-D]ISOXAZOLE DERIVATIVE WHICH IS USEFUL AS A PRODUCTION INTERMEDIATE OF PYRAZINE CARBOXAMIDE DERIVATIVE

(71) Applicants: FUJIFILM Corporation, Tokyo (JP); Toyama Chemical Co., Ltd., Tokyo (JP)

(72) Inventors: Kouki Nakamura, Ashigarakami-gun (JP); Takeshi Murakami, Ashigarakami-gun (JP); Hiroyuki Naitou, Ashigarakami-gun (JP); Naoyuki Hanaki, Ashigarakami-gun (JP); Katsuyuki Watanabe, Ashigarakami-gun (JP)

(73) Assignees: FUJIFILM Corporation, Tokyo (JP); Toyama Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/886,483

(22) Filed: May 3, 2013

(65) Prior Publication Data
US 2013/0245264 A1    Sep. 19, 2013

Related U.S. Application Data

(63) Continuation of application No. PCT/JP2011/076029, filed on Nov. 11, 2011.

(30) Foreign Application Priority Data

Nov. 12, 2010 (JP) .................. 2010-253414
Nov. 17, 2010 (JP) .................. 2010-256510
Feb. 9, 2011 (JP) .................. 2011-025760

(51) Int. Cl.
*C07D 241/50* (2006.01)
*C07C 239/18* (2006.01)
*C07D 498/04* (2006.01)
*C07C 251/38* (2006.01)
*C07C 255/23* (2006.01)
*C07C 237/06* (2006.01)
*C07D 261/18* (2006.01)
*C07C 255/29* (2006.01)
*C07D 241/18* (2006.01)
*C07D 241/24* (2006.01)

(52) U.S. Cl.
CPC ............ *C07D 498/04* (2013.01); *C07C 239/18* (2013.01); *C07C 251/38* (2013.01); *C07C 255/23* (2013.01); *C07C 237/06* (2013.01); *C07D 261/18* (2013.01); *C07C 255/29* (2013.01); *C07D 241/18* (2013.01); *C07D 241/24* (2013.01)
USPC .................................................... 544/350

(58) Field of Classification Search
CPC ...................................................... C07D 241/50
USPC ........................................................ 544/350
See application file for complete search history.

(56) References Cited

U.S. PATENT DOCUMENTS

| | | | |
|---|---|---|---|
| 6,800,629 B2 | 10/2004 | Egawa et al. | |
| 8,168,789 B2 | 5/2012 | Takamatsu et al. | |
| 2003/0130213 A1 | 7/2003 | Egawa et al. | |
| 2010/0286394 A1 | 11/2010 | Takamatsu et al. | |

FOREIGN PATENT DOCUMENTS

| | | |
|---|---|---|
| CN | 1418220 A | 5/2003 |
| WO | 01/60834 A1 | 8/2001 |
| WO | 2009/041473 A1 | 4/2009 |

OTHER PUBLICATIONS

Journal of Organic Chemistry, 1972, vol. 37, #15, pp. 2498-2502.
Journal of Organic Chemistry, 1988, vol. 53, #9, pp. 2052-2055.
*Shin Jikken Jikken Kagaku Koza* (New Experimental Chemistry Course), vol. 14, pp. 1151-1154 (edited by the Chemical Society of Japan, 1977) with English translation.
International Search Report dated Feb. 7, 2012, in Application No. PCT/JP2011/076029.
International Preliminary Report on Patentability dated May 23, 2013 in PCT/JP2011/076029.
Office Action from the State Intellectual Property Office of the People's Republic of China issued Aug. 22, 2014 in a counterpart Chinese Patent Application No. 201180053816.5.
Clinton, R. O. et al., "The Rearrangement of Benzisoxazole-3-Carboxylates," J. Am. Chem. Soc., vol. 74, May 5, 1952, pp. 2226-2237.

*Primary Examiner* — Douglas M Willis
(74) *Attorney, Agent, or Firm* — Sughrue Mion, PLLC

(57) ABSTRACT

The object of the present invention is to provide a compound which is useful as a production intermediate of pyrazine carboxamide derivative such as 6-fluoro-3-hydroxy-2-pyrazine carboxamide. The present invention provides a pyrazino [2,3-d]isoxazole derivative represented by the formula (I):

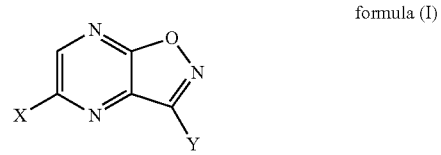

formula (I)

wherein X represents a halogen atom, a hydroxyl group or a sulfamoyloxy group, and Y represents —C(=O)R or —CN; wherein R represents a hydrogen atom, an alkoxy group an aryloxy group, an alkyl group, an aryl group or an amino group.

9 Claims, No Drawings

PYRAZINO[2,3-D]ISOXAZOLE DERIVATIVE WHICH IS USEFUL AS A PRODUCTION INTERMEDIATE OF PYRAZINE CARBOXAMIDE DERIVATIVE

BACKGROUND OF THE INVENTION (1) Field of the Invention

The present invention relates to a pyrazino[2,3-d]isoxazole derivative that is useful as a production intermediate or the like of 6-fluoro-3-hydroxy-2-pyrazine carboxamide (hereinafter referred to as "T-705") useful for treatment such as prevention and therapy of influenza virus infection, and a method for producing the same. In addition, the present invention relates to a method for producing a pyrazinecarbonitrile derivative and a pyrazinecarboxamide derivative using the pyrazino[2,3-d]isoxazole derivative.

(2) Description of Related Art

T-705 is a compound useful for the prevention, treatment and the like of virus infection, and particularly, influenza virus infection. It has been known that T-705 is produced from, for example, 6-fluoro-3-hydroxy-2-pyrazinecarbonitrile (hereinafter referred to as T-705A) (Patent Documents 1 and 2). Patent Document 2 describes that T-705A can be efficiently isolated in the form of salts with various amines.

Examples of a known production method of T-705A includes: (1) a method comprising allowing 3,6-difluoro-2-pyrazinecarbonitrile to react with benzyl alcohol and then debenzylating the reaction product; (2) a method comprising allowing 3,6-difluoro-2-pyrazinecarbonitrile to react with water; and (3) a method comprising allowing 3,6-difluoro-2-pyrazinecarbonitrile to react with carboxylate and then generating T-705A by hydrolysis (Patent Documents 1 and 2).

However, since 3,6-difluoro-2-pyrazinecarbonitrile has high skin irritancy, and easily vaporizes due to low-molecular-weight liquid, it has had a manufacturing problem in that it requires special equipment and careful handling.

Moreover, with regard to the synthesis of pyrazino[2,3-d]isoxazole having a carbonyl group at position 3, examples described in Non-Patent Documents 1 and 2 have been known. However, the pyrazino[2,3-d]isoxazole of the present invention cannot be synthesized by such synthetic methods.

PRIOR ART DOCUMENTS

Patent Documents

Patent Document 1: International Publication WO01/60834
Patent Document 2: International Publication WO09/41473

Non Patent Documents

Non Patent Document 1: Journal of Organic Chemistry, 1972, Vol. 37, #15, pp. 2498-2502
Non Patent Document 2: Journal of Organic Chemistry, 1988, Vol. 53, #9, pp. 2052-2055

BRIEF SUMMARY OF THE INVENTION

Object to be Solved by the Invention

It is an object of the present invention to provide a production intermediate of T-705 and a method for producing the same, which provides high safety and ease in handling, and to further provide a method for safely and easily producing T-705 and the like.

Means for Solving the Object

Thus, the present invention provides the following [1] to [15].

[1] A pyrazino[2,3-d]isoxazole derivative represented by the following formula (I):

[Chem. 1]

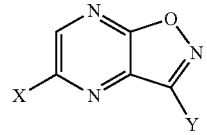

formula (I)

wherein X represents a halogen atom, a hydroxyl group or a sulfamoyloxy group, and Y represents —C(=O)R or —CN; wherein R represents a hydrogen atom, an alkoxy group, an aryloxy group, an alkyl group, an aryl group or an amino group; wherein the sulfamoyloxy group, alkoxy group, aryloxy group, alkyl group, aryl group and amino group may be optionally substituted.

[2] The pyrazino[2,3-d]isoxazole derivative according to [1], wherein Y represents —C(=O)R where R represents an alkoxy group or an amino group, and the alkoxy group and amino group may be optionally substituted.

[3] The pyrazino[2,3-d]isoxazole derivative according to [1] or [2], wherein X represents a hydroxyl group, a chlorine atom or a fluorine atom.

[4] The pyrazino[2,3-d]isoxazole derivative according to [1], wherein X represents a fluorine atom or a chlorine atom, and Y represents —C(=O)R where R represents an optionally substituted alkoxy group.

[5] The pyrazino[2,3-d]isoxazole derivative according to [1], wherein X represents a fluorine atom or a chlorine atom, and Y represents —C(=O)R where R represents a methoxy group, an ethoxy group, an n-propoxy group, an isopropoxy group, or an n-butoxy group.

[6] A method for producing a pyrazino[2,3-d]isoxazole derivative represented by the following formula (I-1):

[Chem. 3]

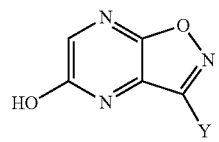

formula (I-1)

wherein Y has the same meanings as those described below, which comprises treating with an acid an isoxazole derivative represented by the following formula (II):

[Chem.2]

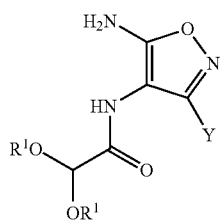

formula (II)

wherein Y represents —C(=O)R or —CN; where R represents a hydrogen atom, an alkoxy group, an aryloxy group, an alkyl group, an aryl group or an amino group; and $R^1$ represents a hydrogen atom or an alkyl group; wherein the alkoxy group, aryloxy group, alkyl group, aryl group and amino group may be optionally substituted.

[7] A method for producing a pyrazinecarbonitrile derivative represented by the following formula (III):

[Chem.5]

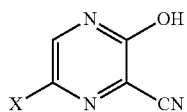

formula (III)

wherein X has the same meanings as those described below, which comprises treating with a base a pyrazino[2,3-d]isoxazole derivative represented by the following formula (I):

[Chem.4]

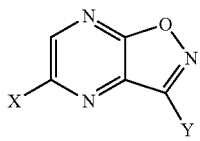

formula (I)

wherein X represents a halogen atom, a hydroxyl group or a sulfamoyloxy group, and Y represents —C(=O)R or —CN; where R represents a hydrogen atom, an alkoxy group an aryloxy group, an alkyl group, an aryl group or an amino group; wherein the sulfamoyloxy group, alkoxy group, aryloxy group, alkyl group, aryl group and amino group may be optionally substituted.

[8] A method for producing a compound represented by the following formula (IV):

[Chem.8]

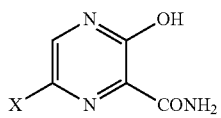

formula (IV)

wherein X has the same meanings as those described below, which comprises
a step of treating with a base a pyrazino[2,3-d]isoxazole derivative represented by the following formula (I):

[Chem. 6]

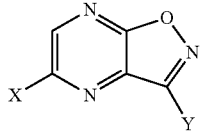

formula (I)

wherein X represents a halogen atom, a hydroxyl group or a sulfamoyloxy group, and Y represents —C(=O)R or —CN; where R represents a hydrogen atom, an alkoxy group an aryloxy group, an alkyl group, an aryl group or an amino group; wherein the sulfamoyloxy group, alkoxy group, aryloxy group, alkyl group, aryl group and amino group may be optionally substituted, so as to produce a compound represented by the following formula (III):

[Chem.7]

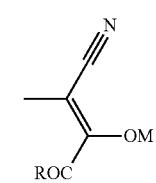

formula (III)

wherein X has the same meanings as describe above, and
a step of adding water to the compound represented by the formula (III).

[9] The production method according to [7] or [8], wherein X represents a fluorine atom and Y represents —C(=O)R where R represents an optionally substituted alkoxy group.

[10] The production method according to [7] or [8], wherein X represents a fluorine atom and Y represents —C(=O)R where R represents a methoxy group, an ethoxy group, an n-propoxy group, an isopropoxy group, or an n-butoxy group.

[11] A compound represented by the following formula (C-2):

[Chem. 9]

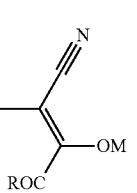

formula (C-2)

wherein $R^1$ represents an alkyl group, $R^3$ represents —CH$_2$CN, the following formula (C-2a):

[Chem.10]

formula (C-2a)

or the following formula (C-2b)

[Chem.11]

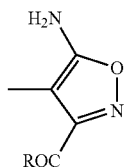

formula (C-2b)

wherein R represents an alkoxy group, M represents H, Li, K or Na; where the alkoxy and alkyl group may be optionally substituted.

[12] A method for producing a pyrazino[2,3-d]isoxazole derivative represented by the following formula (J-4):

[Chem. 13]

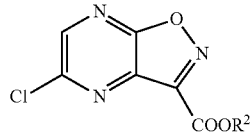

formula (J-4)

wherein $R^2$ has the same meanings as those described below, which comprises allowing a compound represented by the following formula (J-3):

[Chem.12]

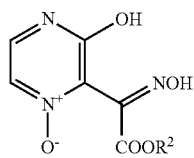

formula (J-3)

wherein $R^2$ represents an alkyl group or an aryl group; wherein the alkyl group and aryl group may be optionally substituted,
to react with a chlorinating agent.

[13] A method for producing a pyrazino[2,3-d]isoxazole derivative represented by the following formula (J-5):

[Chem.15]

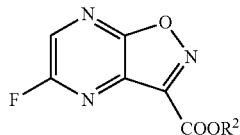

formula (J-5)

wherein $R^2$ represents an alkyl group or an aryl group; wherein the alkyl group and aryl group may be optionally substituted,
which comprises allowing a pyrazino[2,3-d]isoxazole derivative represented by the following formula (J-4):

[Chem.14]

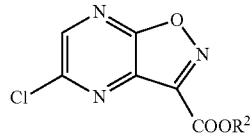

formula (J-4)

wherein $R^2$ represents an alkyl group or an aryl group; wherein the alkyl group and aryl group may be optionally substituted,
to react with a fluorinating agent in the presence of 2,4-dinitrochlorobenzene or 2,4-dinitrofluorobenzene.

[14] A compound represented by the following formula (J-1):

[Chem.16]

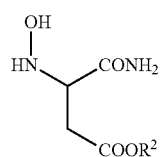

formula (J-1)

wherein $R^2$ represents an alkyl group or an aryl group; wherein the alkyl group and aryl group may be optionally substituted.

[15] A compound represented by the following formula (J-2a):

[Chem.17]

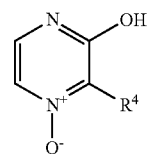

formula (J-2a)

wherein $R^4$ represents —$CH_2COOR^2$, or the following formula (J-2b):

[Chem.18]

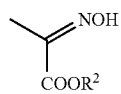

formula (J-2b)

wherein $R^2$ represents an alkyl group or an aryl group; wherein the alkyl group and aryl group may be optionally substituted.

The compound of the formula (I-1), the compound of the formula (III), the compound of the formula (IV), the compound of the formula (J-2) and the compound of the formula (J-3) may exist as tautomer. The present invention includes these tautomers. Further, hydrates, solvates and all crystal forms can be used in the present invention.

Also, the compounds described herein may form a salt.

Salts in such a case may include, for example, commonly known salts produced in the basic group such as amino group or produced in the acidic group such as hydroxyl group or carboxyl group.

Salts produced in the basic group may include, for example, salt produced with mineral acid such as hydrochloric acid, hydrobromic acid, nitric acid, and sulfuric acid; salt with organic carboxylic acid such as formic acid, acetic acid, citric acid, oxalic acid, fumaric acid, maleic acid, succinic acid, malic acid, tartaric acid, aspartic acid, trichloroacetic acid and trifluoroacetic acid; and salts with sulfonic acid such as methanesulfonic acid, benzenesulfonic acid, p-toluenesulfonic acid, mesitylenesulfonic acid and naphthalenesulfonic acid.

Salts produced in the acidic group may include, for example, salts produced with alkaline metals such as sodium and potassium; salts with alkaline earth metals such as calcium and magnesium; ammonium salts; and salts produced with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, and N,N'-dibenzylethylenediamine.

Among the aforementioned salts, preferred salts include pharmacologically acceptable salts.

Effect of the Invention

According to the present invention, T-705 and the like can be safely and easily produced.

DETAILED DESCRIPTION OF THE INVENTION

A compound represented by formula (I) will be described.

In the compound represented by formula (I), X represents a halogen atom, a hydroxyl group or a sulfamoyloxy group. When X represents a halogen atom, examples of the halogen atom include a fluorine atom, a chlorine atom, a bromine atom, or an iodine atom. When X represents a sulfamoyloxy group, the nitrogen atom of the sulfamoyloxy group may be substituted with a hydroxyl group, an amino group, an alkyl group, an aryl group, a heterocyclic group, or an alkylene group with or without the mediation of a heteroatom. The substituent on the nitrogen atom contains preferably 0 to 10, more preferably 2 to 8, and most preferably 2 to 6 carbon atoms. Such a group may further have one or more substituents. As such substituents, those listed in a substituent group A as described later are preferable. Examples of a sulfamoyloxy group which may be optionally substituted include a sulfamoyloxy group, an N,N-dimethylsulfamoyloxy group, an N,N-diethylsulfamoyloxy group, and a morpholinosulfonyloxy group.

X represents preferably a fluorine atom, a chlorine atom, a bromine atom or a hydroxyl group, more preferably a fluorine atom, a chlorine atom or a hydroxyl group, and most preferably a fluorine atom.

Y represents —C(=O)R or —CN. Herein, R represents a hydrogen atom, an alkoxy group, an aryloxy group, an alkyl group, an aryl group or an amino group. When R represents an alkoxy group, it is preferably a linear, branched or cyclic alkoxy group containing 1 to 10 carbon atoms. The alkoxy group contains more preferably 1 to 8, and most preferably 1 to 6 carbon atoms. The alkoxy group may further have one or more substituents. As such substituents, those listed in the substituent group A are preferable. Examples of the alkoxy group which may be optionally substituted include a methoxy group, an ethoxy group, an n-propoxy group, an isopropoxy group, a 2-methoxyethoxy group, an n-butoxy group, an isobutoxy group, a t-butoxy group, an isoamyloxy group, an n-amyloxy group, a neopentyloxy group, an n-hexyloxy group, a cyclohexyloxy group, a benzyloxy group, and a 2-ethylhexyloxy group.

When R represents an aryloxy group, an aryloxy group containing 6 to 12 carbon atoms is preferable, an aryloxy group containing 6 to 10 carbon atoms is more preferable, and an aryloxy group containing 6 to 8 carbon atoms is most preferable. The aryloxy group may further have one or more substituents. As such substituents, those listed in the substituent group A are preferable. Examples of the aryloxy group which may be optionally substituted include a phenoxy group, a 4-methoxyphenoxy group, a 4-dimethylaminophenoxy group, a 3-methylphenoxy group, a 2,6-dimethylphenoxy group, and a 4-t-amylphenoxy group.

When R represents an alkyl group, it is preferably a linear, branched or cyclic alkyl group containing 1 to 10 carbon atoms. The alkyl group contains more preferably 1 to 8, and most preferably 1 to 6 carbon atoms. The alkyl group may further have one or more substituents. As such substituents, those listed in the substituent group A are preferable. Examples of the alkyl group include a methyl group, an ethyl group, an n-propyl group, an isopropyl group, a t-butyl group, an isobutyl group, an n-butyl group, an n-pentyl group, a cyclopentyl group, a cyclohexyl group, and a 1-ethylpropyl group.

When R represents an aryl group, it is preferably an aryl group containing preferably 6 to 12, more preferably 6 to 10, and most preferably 6 to 8 carbon atoms. The aryl group may further have one or more substituents. As such substituents, those listed in the substituent group A are preferable. Examples of the aryl group which may be optionally substituted include a phenyl group, a 4-chlorophenyl group, a 4-methoxyphenyl group, a 3,4-dimethylphenyl group, and a 4-fluorophenyl group.

When R represents an amino group, the amino group may be substituted with a hydroxyl group, an amino group, an alkyl group, an aryl group, a heterocyclic group, or an alkylene group with or without the mediation of a heteroatom. The substituent on the amino group contains preferably 0 to 10, more preferably 2 to 8, and most preferably 2 to 6 carbon atoms. The substituent may further have one or more substituents. As such substituents, those listed in the substituent group A are preferable. Examples of the amino group which may be optionally substituted include an amino group, an N,N-dimethylamino group, an N,N-diethylamino group, an N,N-diisopropylamino group, an N,N-dipropylamino group, a morpholino group, a piperidino group, a 4-methylpiperazino group, a pyrrolidino group, and an N-methyl-N-phenylamino group.

Y preferably represents —C(=O)R wherein R is an alkoxy group.

Substituent group A: an alkyl group containing 1 to 10 carbon atoms, an alkenyl group containing 2 to 10 carbon atoms, an alkynyl group containing 2 to 10 carbon atom, an alkoxy group containing 1 to 10 carbon atoms, an aryloxy group containing 6 to 10 carbon atoms, a halogen atom, an aryl group containing 6 to 10 carbon atoms, a hydroxyl group, an amino group, an acylamino group containing 1 to 10 carbon atoms, an alkylsulfonylamino group containing 1 to 10 carbon atoms, a carbamoyl group containing 1 to 10 carbon atoms, a sulfamoyl group containing 0 to 10 carbon atoms, a carboxyl group, an alkoxycarbonyl group containing 2 to 10 carbon atoms, an acyloxy group containing 2 to 12 carbon atoms, a heterocyclic group, a cyano group, and a nitro group.

Examples of the alkenyl group containing 2 to 10 carbon atoms include a vinyl group, an allyl group, a propenyl group, an isopropenyl group, a butenyl group, an isobutenyl group, a 1,3-butadienyl group, a pentenyl group, a hexenyl group, a heptenyl group, and an octenyl group.

Examples of the alkynyl group containing 2 to 10 carbon atoms include an ethynyl group, a propynyl group, a butynyl group, a pentynyl group, a hexynyl group, a heptynyl group, and an octynyl group.

Examples of the acylamino group containing 1 to 12 carbon atoms include an acetylamino group, a propionylamino group, a benzoylamino group, and a naphthoylamino group.

Examples of the alkylsulfonylamino group containing 1 to 10 carbon atoms include a methanesulfonylamino group, a benzenesulfonylamino group, and a toluenesulfonylamino group.

Examples of the carbamoyl group containing 1 to 10 carbon atoms include a carbamoyl group, an N,N-dimethylcarbamoyl group, an N,N-diethylcarbamoyl group, and a morpholinocarbonyl group.

Examples of the sulfamoyl group containing 0 to 10 carbon atoms include a sulfamoyl group, an N,N-dimethylsulfamoyl group, an N,N-diethylsulfamoyl group, and a morpholinosulfonyl group.

Examples of the alkoxycarbonyl group containing 2 to 10 carbon atoms include a methoxycarbonyl group, an ethoxycarbonyl group, an n-propoxycarbonyl group, an isopropoxycarbonyl group, a 2-methoxyethoxycarbonyl group, an n-butoxycarbonyl group, an isobutoxycarbonyl group, and a t-butoxycarbonyl group.

Examples of the acyloxy group containing 2 to 12 carbon atoms include an acetyloxy group, a propionyloxy group, a benzoyloxy group, and a naphthoyloxy group.

Examples of the heterocyclic group include a pyrrolyl group, a pyrrolinyl group, a pyrrolidinyl group, a piperidinyl group, a piperazinyl group, an imidazolyl group, a pyrazolyl group, a pyridyl group, a tetrahydropyridyl group, a pyridazinyl group, a pyrazinyl group, a pyrimidinyl group, a tetrazolyl group, an imidazolinyl group, an imidazolidinyl group, a pyrazolinyl group, a pyrazolidinyl group, a furyl group, a pyranyl group, a thienyl group, an oxazolyl group, an oxadiazolyl group, an isoxazolyl group, a morpholinyl group, a thiazolyl group, an isothiazolyl group, a thiadiazolyl group, a thiomorpholinyl group, a thioxanyl group, a pyrrol-1-yl group, a pyrrolin-1-yl group, a pyrrolidin-1-yl group, a piperidin-1-yl group, a piperazin-1-yl group, an imidazol-1-yl group, a pyrazol-1-yl group, a tetrazol-1-yl group, an imidazolin-1-yl group, an imidazolidin-1-yl group, a pyrazolin-1-yl group, a pyrazolidin-1-yl group, a morpholin-4-yl group, a thiomorpholin-4-yl group, an indolyl group, an indolinyl group, a 2-oxoindolinyl group, an isoindolyl group, an indolizinyl group, a benzimidazolyl group, a benzotriazolyl group, an indazolyl group, a quinolyl group, a tetrahydroquinolyl group, a tetrahydroisoquinolinyl group, a quinolizinyl group, an isoquinolyl group, a phthalazinyl group, a naphthyridinyl group, a quinoxalinyl group, a dihydroquinoxalinyl group, a quinazolinyl group, a cinnolinyl group, a quinuclidinyl group, a pyrrolopyridyl group, a 2,3-dihydrobenzopyrrolyl group, a benzofuranyl group, an isobenzofuranyl group, a chromenyl group, a chromanyl group, an isochromanyl group, a benzo-1,3-dioxolyl group, a benzo-1,4-dioxanyl group, a 2,3-dihydrobenzofuranyl group, a benzothienyl group, a 2,3-dihydrobenzothienyl group, a benzomorpholinyl group, a benzomorpholonyl group, a benzothiazolyl group, a benzothiadiazolyl group, an indol-1-yl group, an indolin-1-yl group, an isoindol-2-yl group, a benzimidazol-1-yl group, a benzotriazol-1-yl group, a benzotriazol-2-yl group, an indazol-1-yl group, a benzomorpholin-4-yl group, a thianthrenyl group, a xanthenyl group, a phenoxathiinyl group, a carbazolyl group, a 13-carbolinyl group, a phenanthridinyl group, an acridinyl group, a perimidinyl group, a phenanthrolinyl group, a phenazinyl group, a phenothiazinyl group, and a phenoxazinyl group.

Examples of the alkyl group containing 1 to 10 carbon atoms, the alkoxy group containing 1 to 10 carbon atoms, the aryloxy group containing 6 to 10 carbon atoms, the halogen atom, the aryl group containing 6 to 10 carbon atoms, and the amino group include those described with regard to the substituent in the descriptions of the formula (I).

The substituents included in the substituent group A may be further substituted with one or more substituents selected from the substituent group A.

From the viewpoint of the usefulness of the present compound as a production intermediate of T-705A and T-705, it is preferable that, in the formula (I), X be a fluorine atom, a chlorine atom or a hydroxyl group and Y be —C(=O)R wherein R represents an alkoxy group or an amino group, wherein the alkoxy group and the amino group may be substituted; it is more preferable that X be a fluorine atom, a chlorine atom or a hydroxyl group and Y be —C(=O)R wherein R represents an optionally substituted alkoxy group; it is further preferable that X be a fluorine atom and Y be —C(=O)R wherein R represents an optionally substituted alkoxy group; and it is most preferable that X be a fluorine atom and Y be —C(=O)R wherein R represents a methoxy group, an ethoxy group, an n-propoxy group, an isopropoxy group or an n-butoxy group.

Next, the compounds represented by formula (II), formula (I-1), formula (III) and formula (IV) will be described.

The definitions and preferred ranges of X and Y in the formula (II), formula (1-1), formula (III) and formula (IV) are the same as those described for the formula (I).

In the formula (II), 1e represents a hydrogen atom or an alkyl group, where the alkyl group may be optionally substituted. When $R^1$ represents an alkyl group, it is preferably a linear, branched or cyclic alkyl group containing 1 to 10 carbon atoms. The alkyl group contains more preferably 1 to 8, and most preferably 1 to 6 carbon atoms. The alkyl group may further have one or more substituents. As such substituents, those listed in the substituent group A are preferable. Examples of the alkyl group include a methyl group, an ethyl group, an n-propyl group, an isopropyl group, a t-butyl group, an isobutyl group, an n-butyl group, an n-pentyl group, a cyclopentyl group, a cyclohexyl group, and a 1-ethylpropyl group. $R^1$ is preferably a methyl group or an ethyl group.

The compound represented by the formula (I) and the compound represented by formula (II) can be synthesized by the scheme as described below. In the formula as shown below, the definitions and preferred ranges of R and $R^1$ are the same as those described for the formula (I) or the formula (II), and M represents H, Li, K or Na.

[Chem. 19]

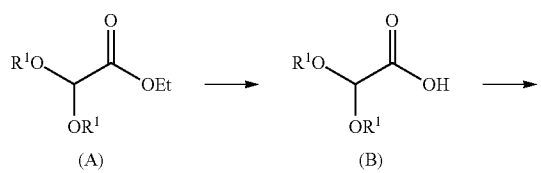

(A)        (B)

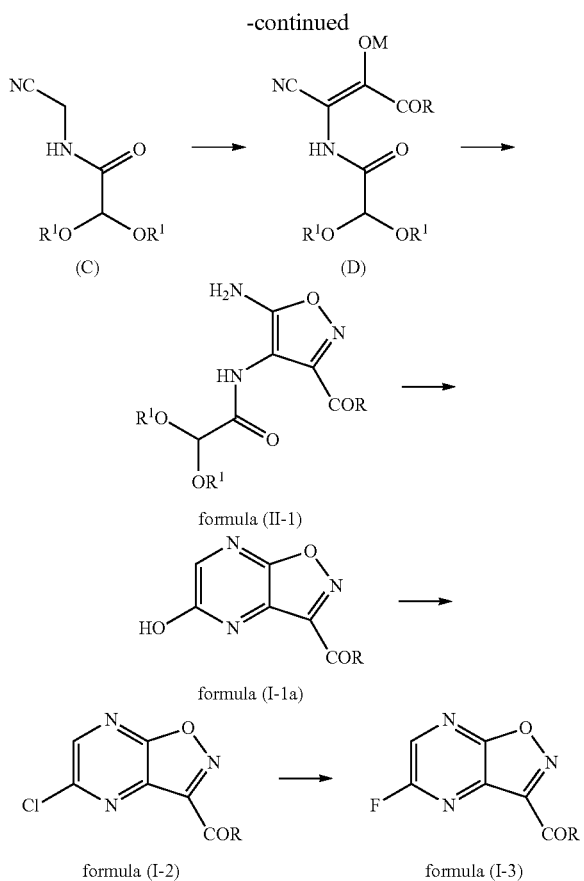

formula (II-1)

formula (I-1a)

formula (I-2)  formula (I-3)

An acetic acid ester (A) is hydrolyzed to obtain a carboxylic acid (B). In this reaction, various types of solvents can be used as solvent. In general, water, or a mixed solvent of water and an organic solvent miscible with the water, can be used. As bases, various types of inorganic bases or organic bases can be used. Metal hydroxides, such as sodium hydroxide, lithium hydroxide or potassium hydroxide, are preferable. A reaction temperature from −20 to 100° C. is preferably applied. The reaction temperature is more preferably from 0 to 80° C.

The obtained carboxylic acid (B) is allowed to react with aminoacetonitrile in a basic to neutral range, so as to convert it to an amide (C). Examples of a condensing agent used during this reaction include: carbodiimides such as dicyclohexylcarbodiimide or 1-ethyl-3-(3-dimethylaminopropyl) carbodiimide hydrochloride; activators such as carbonyldiimidazole or N,N'-disuccinimidyl carbonate; and cationic dehydration-condensation agents such as 2-chloro-1-methyl pyridinium iodide, 2-chloro-1,3-dimethyl imidazolinium chloride or chloro-N,N,N',N'-tetramethyl formamidinium hexafluorophosphonate. Also, there can be applied a method comprising allowing the obtained compound to react with acid halides such as chlorocarbonic ester or methanesulfonyl chloride to obtain a mixed acid anhydride, and then allowing it to react with acetonitrile. The reaction temperature is different depending on a condensing agent used. In general, it is preferably from −20° C. to room temperature. The solvent that can be used herein is not particularly limited so long as it does not affect the reaction, and examples there include: nitriles such as acetonitrile; aromatic hydrocarbons such as benzene, toluene or xylene; halogenated hydrocarbons such as chloroform, methylene chloride or 1,2-dichloroethane; amides such as N,N-dimethylformamide, N,N-dimethylacetamide, N-methylpyrrolidone and N-ethyl pyrrolidone; esters such as ethyl acetate, isopropyl acetate or butyl acetate; sulfoxides such as dimethyl sulfoxide; sulfolane; and tetrahydrofuran. These solvents may be used in combination. Also, a reaction is also preferably carried out in a two-phase system of an organic solvent and water.

A condensation reaction from amide (C) to amide (D) can be carried out by reacting the amide (C) with an oxalic diester or the like, using metal alkoxide as a base, in a solvent such as tetrahydrofuran or toluene. The reaction temperature is preferably from 0 to 60° C., and more preferably from 10 to 40° C. A reaction product is generally precipitated in the form of a salt from the reaction system. This salt may be collected by filtration and may be then used in the subsequent reaction, or it may be directly used in the subsequent reaction without performing special operations. Otherwise, the filtrated crystal may be neutralized and the obtained product may be then used in the subsequent reaction.

Conversion of amide (D) to isoxazole (formula (II-1)) can be achieved firstly by reacting amide (D) with hydroxylamine to form an oxime and carrying out a ring closure reaction thereon with a catalyst such as an acid or a base. As hydroxylamine, any one of an aqueous solution of 50% hydroxylamine, hydroxylamine hydrochloride, and hydroxylamine sulfate can be used. As a solvent, dimethyl sulfoxide, methanol, ethanol, water or the like is preferably used. The reaction temperature is preferably from 0 to 100° C., and more preferably from room temperature to 80° C.

The compound represented by formula (II-1) is treated with an acid, so as to produce 5-hydroxypyrazino[2,3-d]isoxazole (formula (I-1a)). Examples of an acid used herein include: proton acids such as hydrogen chloride, sulfuric acid, p-toluenesulfonic acid, camphorsulfonic acid, trifluoroacetic acid or trifluoromethanesulfonic acid; and Lewis acids such as aluminum chloride, zinc chloride or iron chloride. The acids that are preferably used herein are proton acids. Of these, hydrogen chloride, sulfuric acid and p-toluenesulfonic acid are more preferable, and p-toluenesulfonic acid is particularly preferable. The amount of the acid used as a catalyst is preferably 0.0001 to 1000 times, more preferably 0.001 to 100 times, and most preferably 0.01 to 10 times the molar amount of the compound represented by the formula (II-1).

The type of a solvent used herein is not particularly limited, as long as it does not affect the reaction. Examples of the solvent include: nitriles such as acetonitrile; aromatic hydrocarbons such as benzene, toluene or xylene; ethers such as dioxane, tetrahydrofuran or ethylene glycol dimethyl ether; ketones such as acetone or 2-butanone; alcohols such as methanol, ethanol or 2-propanol; amides such as N,N-dimethylformamide or N,N-dimethylacetamide; carboxylic acids such as acetic acid, propionic acid or trifluoroacetic acid; esters such as ethyl acetate or isopropyl acetate; and sulfoxides such as dimethyl sulfoxide. These solvents may be used in combination. Examples of a preferred solvent include aromatic hydrocarbons, ethers, alcohols, carboxylic acids, esters, and sulfoxides. Of these, carboxylic acids, alcohols and esters are more preferable, and acetic acid is further preferable. Such a solvent may also act as an acid catalyst.

The amount of a solvent used is not particularly limited. The solvent is used in an amount of preferably 1 to 50 times (v/w), and more preferably 1 to 15 times (v/w) the amount of the compound represented by the formula (II-1).

The reaction temperature is different depending on an acid catalyst and a solvent used. It is preferably 200° C. or lower, and more preferably from 0 to 150° C. The reaction time is not particularly limited. It is preferably 5 minutes to 50 hours, more preferably 5 minutes to 24 hours, and particularly preferably 5 minutes to 5 hours.

In this reaction, R in the compound of the formula (II-1) is particularly preferably an alkoxy group.

Conversion of the compound of the formula (I-1a) to 5-chloropyrazino[2,3-d]isoxazole (formula (I-2)) can be achieved using various types of chlorinating agents, with or without a solvent. The chlorinating agent can be selected from among phosphoryl chloride, phosphorus pentachloride, phosphorus trichloride and the like. When a solvent is used, preferred examples of the solvent include N,N-dimethylformamide, N,N-dimethylacetamide, acetonitrile, sulfolane, N-methylpyrrolidone, ethyl acetate, and a mixed solvent thereof. As necessary, triethylamine, pyridine, triethylamine hydrochloride and the like may be added. The reaction temperature is preferably from room temperature to 130° C., and in general, it is more preferably from 50 to 110° C.

In a reaction of converting the compound of the formula (I-2) to 5-fluoropyrazino[2,3-d]isoxazole (formula (I-3)), various types of fluorinating reagents can be used as fluorinating agents. Preferred examples of the fluorinating reagent include potassium fluoride, cesium fluoride, tetra-n-butylammonium fluoride, tetramethylammonium fluoride, and tetraphenylphosphonium fluoride. Of these, potassium fluoride and cesium fluoride are preferable. With regard to potassium fluoride, spray-dried potassium fluoride is particularly preferable. The fluorinating agent is added in an amount of preferably 1 to 10 times, more preferably 1.1 to 5 times, and most preferably 1.1 to 3 times the molar amount of a reaction substrate. A dehydration fluorinating agent such as 2,2-difluoro-1,3-dimethylimidazoline (DFI) or 1,1,2,3,3,3-hexafluoro-1-diethylaminopropane (Ishikawa's Reagent), may also be added. Preferred examples of a solvent include aprotic solvents, such acetonitrile, N,N-dimethylformamide, N,N-dimethylacetamide, sulfolane, dimethyl sulfoxide, N-methylpyrrolidone, N-ethyl pyrrolidone or tetrahydrofuran. Of these, acetonitrile, N,N-dimethylformamide, N,N-dimethylacetamide, sulfolane and dimethyl sulfoxide are more preferable, and acetonitrile, N,N-dimethylformamide and dimethyl sulfoxide are further preferable. The amount of a solvent used is not particularly limited, and is preferably 0.5 to 20 times (v/w), more preferably 1 to 10 times (v/w), and most preferably 1 to 3 times (v/w) the volume of the compound of the formula (I-2). The upper limit of the reaction temperature is changed depending on the boiling point of a solvent. In general, it is preferably from 0 to 130° C., more preferably from room temperature to 110° C., and most preferably from 50 to 100° C. It is preferable that the concentration of water content in the reaction system is low. The concentration of the water content is more preferably 0.01 to 1000 ppm, further preferably 0.01 to 500 ppm, and most preferably 0.01 to 300 ppm. In order to reduce the water content in the reaction system, various types of dehydration operations may be carried out before the reaction. For example, it is preferable that a fluorinating reagent to be used is dried by heating (80° C. to 500° C.) and vacuum suction (0.001 to 100 ton). Moreover, when a high boiling point solvent (dimethyl sulfoxide, sulfolane, N-methylpyrrolidone, N,N-dimethylformamide, etc.) is used, azeotropic dehydration is preferably carried out using toluene or xylene. Moreover, it is also preferable to distill away a high boiling point solvent under reduced pressure, so as to reduce water content in the system. Furthermore, for the purpose of reducing water content in the system, molecular sieves or the like can be added. In this operation, molecular sieves, which have been dehydrated and dried at a high temperature, are preferable.

For the purpose of promoting the reaction, cationic phase transfer catalysts such as tetra-n-butylammonium chloride, tetra-n-butylammonium bromide, tetraphenylphosphonium chloride, tetramethylammonium chloride or trimethylbenzylammonium bromide, and nonionic phase transfer catalysts such as 18-crown-6, polyethylene glycol 400, polyethylene glycol 1000 or tris(2-(2-methoxyethoxy)ethyl)amine, can be preferably used. The reaction time is preferably 5 minutes to 50 hours, more preferably 10 minutes to 10 hours, and most preferably 15 minutes to 5 hours.

When a compound of the formula (J-5) is synthesized from a compound of the formula (J-4) as described later, 2,4-dinitrochlorobenzene or 2,4-dinitrofluorobenzene is preferably added into the reaction mixture. Using these additives, the amount of black tar component generated as a result of a fluorination reaction can be reduced, and thus, the quality of the compound of the formula (J-5), or further, the compound obtained in the subsequent process, can be improved.

[Chem.20]

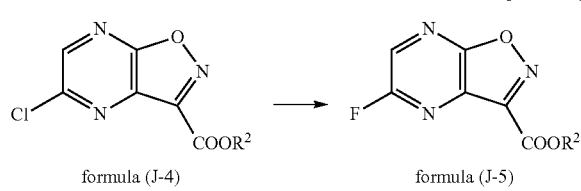

formula (J-4)    formula (J-5)

2,4-Dinitrochlorobenzene or 2,4-dinitrofluorobenzene is added in an amount of preferably 0.001 to 10 times, more preferably 0.01 to 1 times, and most preferably 0.01 to 0.2 times the molar amount of the compound of the formula (J-4).

Further, it is possible to convert the compound of the formula (I-1a) to the compound of the formula (I-3) without mediating the compound of the formula (I-2) according to a method of allowing 2,2-difluoro-1,3-dimethylimidazoline (DFI) on the compound of the formula (I-1a) in acetonitrile.

Still further, it is also possible to convert the compound of the formula (I-1a) to the compound of the formula (I-3) by converting the group at position 5 of the compound of the formula (I-1a) to a leaving group such as a sulfamoyloxy group according to a method of allowing the compound of the formula (I-1a) to react with sulfamoyl chloride in the presence of a base, and then by substituting the group at position 5 using potassium fluoride, tetrabutylammonium fluoride or the like as a fluorine anion source.

That is to say, a pyrazino[2,3-d]isoxazole derivative having, at position 5 thereof, a group substitutable with a fluorine atom or a group that can be easily induced to such a group, is also important as a production intermediate of T-705A.

When Y is —C(═O)R and R is an amino group in the formula (I), the compound can be synthesized by a method of allowing the compound represented by the formula (I) wherein R is an alkoxy group to react with amine. In this reaction, it is preferable to add a suitable base (for example, triethylamine, diisopropylethylamine, pyridine, potassium carbonate or sodium bicarbonate). The type of a solvent used herein is not particularly limited, as long as it does not affect the reaction. Examples of the solvent include: nitriles such as acetonitrile; aromatic hydrocarbons such as benzene, toluene or xylene; ethers such as dioxane, tetrahydrofuran or ethylene glycol dimethyl ether; ketones such as acetone or 2-butanone; alcohols such as methanol, ethanol or 2-propanol; amides such as N,N-dimethylformamide or N,N-dimethylacetamide; esters such as ethyl acetate or isopropyl acetate; and sulfoxides such as dimethyl sulfoxide. These solvents may be used in combination. Examples of a preferred solvent include aromatic hydrocarbons, ethers, alcohols, esters, and sulfoxides. The amount of a solvent used is not particularly limited. The solvent is used in an amount of preferably 1 to 50 times (v/w), and more preferably 1 to 15 times (v/w) the amount of the compound of the formula (I). The reaction temperature is preferably 200° C. or lower, and more preferably from 0 to 150° C. The reaction time is not particularly limited. It is preferably 5 minutes to 50 hours, more preferably 5 minutes to 24 hours, and particularly preferably 5 minutes to 5 hours.

Among the compounds represented by the formula (I), a compound represented by a formula (J-4) as shown below can be synthesized by the following scheme, for example.

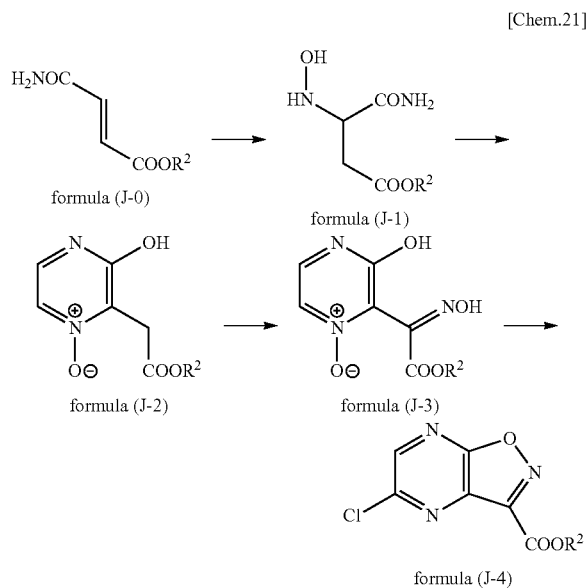

[Chem.21]

In the compounds of the formulae (J-0) to (J-4), $R^2$ represents an alkyl group or an aryl group. The alkyl group and aryl group may be optionally substituted. It is to be noted that the same applies to $R^2$ in the compound of the above-described formula (J-5).

When $R^2$ represents an alkyl group, it is preferably a linear, branched or cyclic alkyl group containing 1 to 10 carbon atoms. The alkyl group contains more preferably 1 to 8, and most preferably 1 to 6 carbon atoms. The alkyl group may further have substituent(s). As such substituents, those listed in the substituent group A are preferable. Examples of the alkyl group which may be optionally substituted include a methyl group, an ethyl group, an n-propyl group, an isopropyl group, a 2-methoxyethyl group, a t-butyl group, an isobutyl group, an n-butyl group, an isoamyl group, n-amyl group, a neopentyl group, an n-hexyl group, a cyclohexyl group, a benzyl group, and a 2-ethylhexyl group.

When $R^2$ represents an aryl group, it is preferably an aryl group containing preferably 6 to 12, more preferably 6 to 10, and most preferably 6 to 8 carbon atoms. The aryl group may further have substituent(s). As such substituents, those listed in the substituent group A are preferable. Examples of the aryl group which may be optionally substituted include a phenyl group, a 4-methoxyphenyl group, a 4-dimethylamino phenyl group, 3-methylphenyl group, 2,6-dimethylphenyl group, and a 4-t-aminophenyl group.

In the present invention, $R^2$ in the compounds of the formulae (J-0) to (J-4) is preferably an alkyl group containing 1 to 6 carbon atoms. A methyl group, an ethyl group, an n-propyl group, an isopropyl group, an n-butyl group, an isobutyl group, a sec-butyl group, and a t-butyl group are particularly preferable.

In the compound of formula (J-3), the hydroxyl group of the oxime may adopt both anti- and syn-isomer structures. In the present invention, it may be either one isomer or a mixture thereof.

The compound of the formula (J-0) can be synthesized by a known method. For example, a maleic anhydride is allowed to react with alcohol to synthesize a maleic monoester, it is then induced to an acid chloride using a chlorinating agent such as thionyl chloride, and the acid chloride is then allowed to react with ammonia, so as to convert it to an amide body. Alternatively, the above-described maleic monoester is allowed to react with, for example, methanesulfonyl chloride or chloroformic ester, so as to induce it to a mixed acid anhydride, and the mixed acid anhydride is then allowed to react with ammonia, so as to convert it to an amide body. During these reactions, salts such as ammonium carbonate or ammonium acetate may be used in addition to ammonia. Moreover, as an alternative method, a maleic anhydride is allowed to react with ammonia to synthesize maleic monoamide, and it is then allowed to react with alcohol in the presence of an acid catalyst such as concentrated sulfuric acid to esterify it, so as to obtain the compound of the formula (J-0).

In the present invention, the compound of the formula (J-0) may be either a cis- or trans-isomer.

Conversion of the compound of formula (J-0) to the compound of formula (J-1) can be achieved by conjugate addition of hydroxylamine.

As hydroxylamine, 50% hydroxylamine aqueous solution, hydroxylamine hydrochloride, hydroxylamine sulfate, or the like may be used.

When hydroxylamine hydrochloride or hydroxylamine sulfate is used, various types of organic bases or inorganic bases are preferably added. Examples of a base that can be used herein include triethylamine, pyridine, sodium hydroxide, potassium hydroxide, potassium carbonate, sodium bicarbonate, and sodium phosphate. The base is used in an amount of preferably 0.1 to 10 times, more preferably 0.5 to 2 times, and most preferably 1 to 1.2 times the molar amount of hydroxylamine.

The hydroxylamine is used in an amount of preferably 1 to 10 times, more preferably 1 to 2 times, and most preferably 1 to 1.2 times the molar amount of the compound of the formula (J-0).

The type of a solvent used herein is not particularly limited, as long as it does not affect the reaction. Examples of the solvent include: water; nitriles such as acetonitrile; aromatic hydrocarbons such as benzene, toluene or xylene; ethers such as dioxane, tetrahydrofuran or ethylene glycol dimethyl ether; ketones such as acetone or 2-butanone; alcohols such as methanol, ethanol or 2-propanol; amides such as N,N-dimethylformamide or N,N-dimethylacetamide; esters such as ethyl acetate or isopropyl acetate; and sulfoxides such as dimethyl sulfoxide. These solvents may be used in combination. Examples of a preferred solvent include aromatic hydrocarbons, ethers, alcohols, esters, and sulfoxides. Of these, aromatic hydrocarbons, alcohols and esters are more preferable.

The amount of a solvent used is not particularly limited. The solvent is used in an amount of preferably 1 to 50 times (v/w), more preferably 1 to 10 times (v/w), and most preferably 1 to 3 times (v/w) the amount of the compound of the formula (J-0).

The reaction temperature is different depending on a solvent used. It is preferably from 0 to 130° C., more preferably from room temperature to 100° C., and particularly preferably from room temperature to 50° C.

The reaction time is not particularly limited. It is preferably 5 minutes to 10 hours, more preferably 10 minutes to 5 hours, and particularly preferably 10 minutes to 1 hour.

The compound of the formula (J-1) may be isolated and may be then subjected to the subsequent process. Otherwise, it may be subjected to the subsequent process without being isolated.

Conversion of the compound of the formula (J-1) to the compound of formula (J-2) can be achieved by allowing the compound of the formula (J-1) to react with glyoxal in the presence of an acid or a base. As glyoxal, an inexpensive 40% glyoxal aqueous solution is preferably used. It is also possible to use, for example, an acetal body or a sulfite ion adduct as a product equivalent to glyoxal.

The glyoxal is used in an amount of preferably 1 to 10 times, more preferably 1 to 5 times, and most preferably 1 to 3 times the molar amount of the compound of the formula (J-1).

The type of a solvent used herein is not particularly limited, as long as it does not affect the reaction. Examples of the solvent include: water; nitriles such as acetonitrile; aromatic hydrocarbons such as benzene, toluene or xylene; ethers such as dioxane, tetrahydrofuran or ethylene glycol dimethyl ether; ketones such as acetone or 2-butanone; alcohols such as methanol, ethanol or 2-propanol; amides such as N,N-dimethylformamide or N,N-dimethylacetamide; esters such as ethyl acetate or isopropyl acetate; and sulfoxides such as dimethyl sulfoxide. These solvents may be used in combination. Examples of a preferred solvent include water, nitriles, ethers, ketones, alcohols, and amides. Of these, water, ethers and alcohols are more preferable, and water is most preferable.

The amount of a solvent used is not particularly limited. The solvent is used in an amount of preferably 1 to 50 times (v/w), more preferably 1 to 20 times (v/w), and most preferably 1 to 10 times (v/w) the amount of the compound of the formula (J-1).

For the purpose of improving yield, it is preferable to add an acid or a base in the present reaction. Examples of an acid used herein include: proton acids such as hydrogen chloride, sulfuric acid, p-toluenesulfonic acid, camphorsulfonic acid, trifluoroacetic acid or trifluoromethanesulfonic acid; and Lewis acids such as aluminum chloride, zinc chloride or iron chloride. Of these, proton acids are preferable, and hydrogen chloride, sulfuric acid and acetic acid are more preferable.

As bases, various types of inorganic bases or organic bases can be used. Examples of a preferred inorganic base include sodium bicarbonate, potassium carbonate, sodium carbonate, lithium hydroxide, sodium hydroxide, potassium hydroxide, potassium phosphate, and sodium monohydrogen phosphate. Examples of a preferred organic base include triethylamine, N,N-diisopropylethylamine, pyridine, and picoline.

The acid or a base is used in an amount of preferably 0.01 to 100 times, more preferably 0.1 to 10 times, and most preferably 1 to 5 times the molar amount of the compound of the formula (J-1).

The reaction temperature is different depending on a solvent used. It is preferably from 0 to 130° C., more preferably from room temperature to 100° C., and particularly preferably from 40 to 80° C.

The reaction time is not particularly limited. It is preferably 5 minutes to 10 hours, more preferably 10 minutes to 5 hours, and particularly preferably 30 minutes to 2 hours.

Conversion of the compound of the formula (J-2) to the compound of formula (J-3) can be achieved by allowing the compound of the formula (J-2) to react with nitrite ester in the presence of an acid. As nitrite ester, ethyl nitrite, n-propyl nitrite, isopropyl nitrite, n-butyl nitrite, isobutyl nitrite, t-butyl nitrite, isoamyl nitrite or the like can be used. Of these, isoamyl nitrite is particularly preferable in terms of ready availability.

Moreover, the compound of the formula (J-3) can be obtained also by adding a sodium nitrite aqueous solution to a mixture of the compound of the formula (J-2) and an acid.

The nitrite ester or sodium nitrite is used in an amount of preferably 1 to 10 times, more preferably 1 to 5 times, and most preferably 1 to 3 times the molar amount of the compound of the formula (J-2).

Examples of an acid used herein include: proton acids such as hydrogen chloride, sulfuric acid, acetic acid, p-toluenesulfonic acid, camphorsulfonic acid, trifluoroacetic acid or trifluoromethanesulfonic acid; and Lewis acids such as aluminum chloride, zinc chloride or iron chloride. The acids that are preferably used herein are proton acids. Of these, hydrogen chloride, sulfuric acid and acetic acid are more preferable, and hydrogen chloride is most preferable. When hydrogen chloride is used, acid chloride such as acetyl chloride may be added to alcohols such as ethanol so as to generate hydrogen chloride in a system. The acid is used in an amount of preferably 0.01 to 100 times, more preferably 0.1 to 10 times, and most preferably 1 to 5 times the molar amount of the compound of the formula (J-2).

The type of a solvent used herein is not particularly limited, as long as it does not affect the reaction. Examples of the solvent include: water; nitriles such as acetonitrile; aromatic hydrocarbons such as benzene, toluene or xylene; ethers such as dioxane, tetrahydrofuran or ethylene glycol dimethyl ether; ketones such as acetone or 2-butanone; alcohols such as methanol, ethanol or 2-propanol; amides such as N,N-dimethylformamide or N,N-dimethylacetamide; carboxylic acids such as acetic acid, propionic acid or trifluoroacetic acid; esters such as ethyl acetate or isopropyl acetate; and sulfoxides such as dimethyl sulfoxide. These solvents may be used in combination. Examples of a preferred solvent include water, ethers, alcohols, amides, and carboxylic acids. Of these, ethers, alcohols and carboxylic acids are more preferable, and alcohols are particularly preferable.

The amount of a solvent used is not particularly limited. The solvent is used in an amount of preferably 1 to 50 times (v/w), more preferably 1 to 10 times (v/w), and most preferably 1 to 5 times (v/w) the amount of the compound of the formula (J-2).

The reaction temperature is different depending on a solvent used. It is preferably from 0 to 130° C., more preferably from room temperature to 100° C., and particularly preferably from room temperature to 70° C.

The reaction time is not particularly limited. It is preferably 5 minutes to 10 hours, more preferably 10 minutes to 5 hours, and particularly preferably 30 minutes to 3 hours.

In order to convert the compound of the formula (J-3) to the compound of the formula (J-4), chlorination of a pyrazine ring and formation of an isoxazole ring may be simultaneously carried out, or these two reactions may be carried out stepwise.

In the present reaction, phosphorus oxychloride, thionyl chloride, phosphorus pentachloride, phosphorus trichloride, pyrocatechyl phosphotrichloride, dichlorotriphenylphosphorane and oxalyl chloride are used as a reagent(s), singly or in combination of two or more types. Of these, phosphorus oxychloride and thionyl chloride are more preferably in terms of yield and costs, and phosphorus oxychloride is particularly preferable. The reagent is used in an amount of preferably 1 to 20 times, more preferably 2 to 10 times, and most preferably 2 to 5 times the molar amount of the compound of the formula (J-3).

The type of a solvent used herein is not particularly limited, as long as it does not affect the reaction. Examples of the solvent include: nitriles such as acetonitrile; aromatic hydrocarbons such as benzene, toluene or xylene; ethers such as dioxane, tetrahydrofuran or ethylene glycol dimethyl ether; ketones such as acetone or 2-butanone; amides such as N,N-dimethylformamide, N,N-dimethylacetamide or N-methylpyrrolidone; ureas such as 1,3-dimethyl-2-imidazolidinone; and esters such as ethyl acetate or isopropyl acetate. These solvents may be used in combination. Examples of a preferred solvent include nitriles, aromatic hydrocarbons, ethers, amides, ureas, and esters. Of these, aromatic hydrocarbons and amides are more preferable. For the purpose of increasing the reaction rate, dimethylformamide is preferably added.

The amount of a solvent used is not particularly limited. The solvent is used in an amount of preferably 1 to 50 times (v/w), more preferably 1 to 10 times (v/w), and most preferably 1 to 5 times (v/w) the amount of the compound of the formula (J-3).

The reaction temperature is different depending on a solvent used. It is preferably from 0 to 130° C., more preferably from room temperature to 100° C., and particularly preferably from 50 to 80° C. The reaction time is not particularly limited. It is preferably 5 minutes to 20 hours, more preferably 30 minutes to 10 hours, and particularly preferably 1 to 5 hours.

Next, a reaction of producing a compound of the formula (III) using the compound of the formula (I) will be described. In this reaction, as bases, various types of inorganic bases or organic bases can be used. Examples of a preferred inorganic base include potassium fluoride, cesium fluoride, sodium bicarbonate, potassium carbonate, sodium carbonate, lithium hydroxide, sodium hydroxide, potassium hydroxide, sodium phosphate, potassium phosphate, sodium monohydrogen phosphate, and sodium borate. Examples of a preferred organic base include triethylamine, ethyl(diisopropyl)amine, pyridine, and picoline. More preferred bases include sodium bicarbonate, potassium carbonate, sodium carbonate, sodium hydroxide, potassium hydroxide, sodium phosphate, potassium phosphate, and sodium monohydrogen phosphate.

The base is used in an amount of preferably 0.1 to 100 times, more preferably 0.5 to 30 times, and most preferably 1 to 10 times the molar amount of the compound of the formula (I).

The type of a solvent used herein is not particularly limited, as long as it does not affect the reaction. Examples of the solvent include: water; nitriles such as acetonitrile; aromatic hydrocarbons such as benzene, toluene or xylene; ethers such as dioxane, tetrahydrofuran or ethylene glycol dimethyl ether; ketones such as acetone or 2-butanone; alcohols such as methanol, ethanol or 2-propanol; amides such as N,N-dimethylformamide or N,N-dimethylacetamide; esters such as ethyl acetate or isopropyl acetate; and sulfoxides such as dimethyl sulfoxide. These solvents may be used in combination. As such a solvent, a single use of water, or a use of a mixed solution of water and organic solvents (alcohols, nitriles, ethers or sulfoxides) miscible with the water, is preferable. Moreover, it is also preferable that solvents that are immiscible with water, such as aromatic hydrocarbons, esters or ethers, be used, and that the reaction be carried out in a two-phase system of such an immiscible solvent and water. Furthermore, a solvent miscible with water may be mixed with a solvent immiscible with water, and the thus mixed solvent may be then used. Examples of more preferred solvent include aromatic hydrocarbons, ethers, alcohols, esters, and water. A two-phase system of an aromatic hydrocarbon and water is more preferable. The amount of the solvent used is not particularly limited. The solvent is used in an amount of preferably 1 to 50 times (v/w), and more preferably 1 to 15 times (v/w) the amount of the compound of the formula (I).

The reaction temperature is preferably 200° C. or lower, and more preferably from 0 to 150° C. The reaction time is not particularly limited. It is preferably 5 minutes to 50 hours, more preferably 5 minutes to 24 hours, and particularly preferably 5 minutes to 5 hours.

In such a reaction, the above-described cationic phase transfer catalysts or nonionic phase transfer catalysts can also be used.

In this reaction, it is particularly preferable that X in the compound of the formula (I) be a fluorine atom and Y be —C(=O)R wherein R represents an optionally substituted alkoxy group.

In accordance with the method described in Shin Jikken Kagaku Koza (New Experimental Chemistry Course), Vol. 14, pp. 1151-1154 (edited by the Chemical Society of Japan, 1977), water is added to the compound of the formula (III) (1) under acidic conditions, (2) under basic conditions in the presence or absence of a hyperacid, or (3) under neutral conditions, thereby obtaining the compound of the formula (IV). In this reaction, it is particularly preferable that X be a fluorine atom.

EXAMPLES

Hereinafter, a method for safely and easily producing T-705A and T-705, using the compound of the formula (I) of the present invention as an intermediate, will be described in the following specific examples. It is to be noted that, in the NMR spectral data in the following examples, "s" indicates a singlet, "d" indicates a doublet, "t" indicates a triplet, "q" indicates a quartet, "quint" indicates a quintet, "sep" indicates a septet, "h" indicates a nonuplet, "dd" indicates a quartet with unequal distance, "m" indicates a multiplet, and "br" indicates a broad line.

[Chem.22]

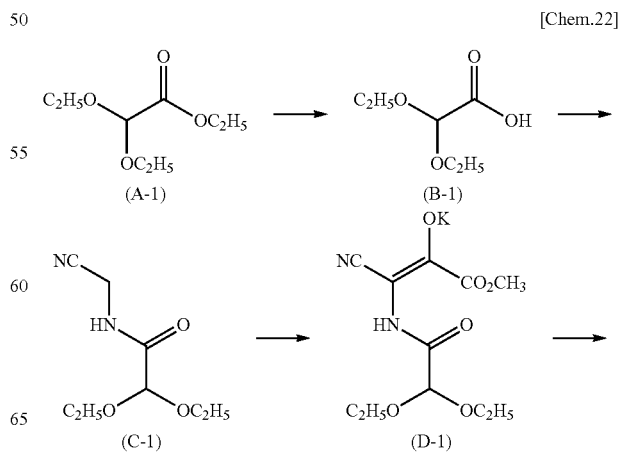

-continued

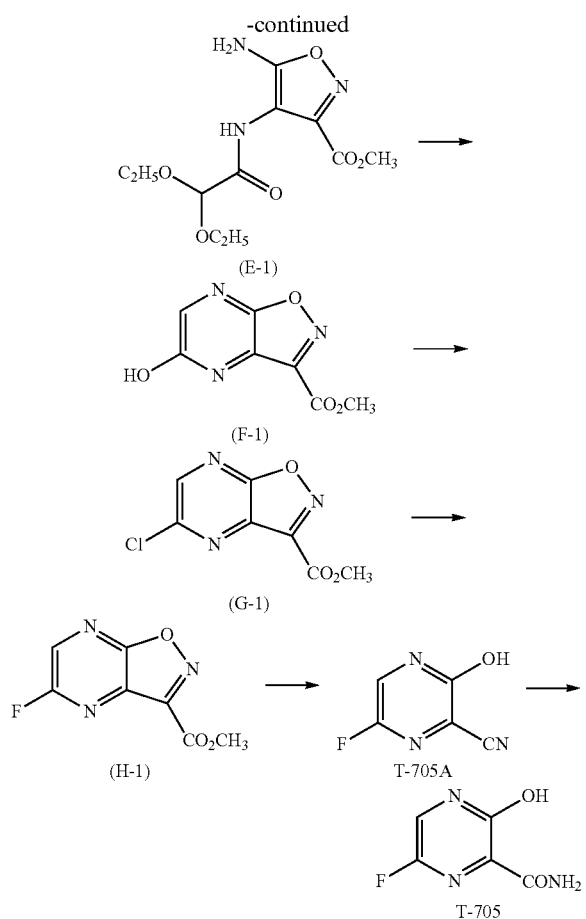

Synthesis Example 1

Synthesis of (B-1)

11.3 L of water and 1090 g of sodium hydroxide were added to a 30-L reaction vessel made of glass, and they were dissolved therein. To the obtained solution, 4000 g of (A-1) (the reagent of Tokyo Chemical Industry Co., Ltd.) was added, and the obtained mixture was then stirred at an internal temperature of 70° C. for 30 minutes. Thereafter, 2270 g of sodium chloride was added to the reaction solution and dissolved therein, and the obtained reaction mixture was then cooled to 0° C. or lower. 2270 mL of concentrated hydrochloric acid was slowly added to the reaction mixture, and 11.3 L of ethyl acetate was then added to the mixture. After completion of liquid separation, an aqueous layer was discarded. 11.3 L of a saturated saline was added to the obtained organic layer, and after completion of liquid separation, an aqueous layer was discarded. The obtained organic layer was concentrated under reduced pressure. To the thus obtained residue, 5.00 L of toluene was added, and the toluene solution was then concentrated under reduced pressure. 5.00 L of toluene was added to the resultant again, followed by vacuum concentration. As a result, 3200 g of light yellow oil (B-1) was obtained. Yield: 95.1%.

$^1$H-NMR (400 MHz, CDCl$_3$) δ value: 9.09 (br, 1H), 4.97 (s, 1H), 3.64-3.77 (m, 4H), 1.28 (t, J=7.1 Hz, 6H)

Synthesis Example 2

Synthesis of (C-1)

1.48 kg (10.0 mol) of (B-1) was dissolved in 7.40 L of acetonitrile, and 1.10 kg (5.25 mol) of aminoacetonitrile sulfate was then added to the obtained solution. While keeping the internal temperature at 5° C. or lower, 1.91 kg (10.0 mol) of 1-ethyl-3-(3-dimethylaminopropyl)carbodiimide hydrochloride was added to the mixture. While keeping the internal temperature at 0° C. to 6° C., 2.07 kg (20.0 mol) of triethylamine was added dropwise to the mixture over 90 minutes. The obtained reaction mixture was left at room temperature overnight. 3.00 L of water was added to the reaction mixture, and the solvent was then distilled away under reduced pressure. 7.40 L of ethyl acetate was added to the residue, and the obtained mixture was then stirred for 10 minutes. Thereafter, the reaction solution was left at rest, and an aqueous layer was then removed. The organic layer was cooled. Subsequently, while keeping the internal temperature at 6° C. or lower, approximately 2.00 L of 1.00 mol/L hydrochloric acid was added thereto, so that the pH of the aqueous layer was adjusted to pH 5. Further, 1.00 L of water was added thereto, and the mixture was then stirred and left at rest, so as to remove the aqueous layer. 3.00 L of a saturated saline was added to the organic layer, and the obtained mixture was then stirred and left at rest, so as to remove the aqueous layer. The solvent was distilled away from the obtained organic layer under reduced pressure, and 2.00 L of toluene was then added to the residue, followed by vacuum distillation. Further, 1.00 L of toluene was added to the resultant, followed by vacuum distillation, so as to obtain 1.11 kg of light brown oil (C-1). Yield: 59.7%.

$^1$H-NMR (CDCl$_3$) δ value: 1.27 (6H, t, J=7.2 Hz), 3.65 (2H, q, J=7.2 Hz), 3.69 (2H, q, J=7.2 Hz), 4.22 (1H, s), 4.23 (1H, s), 4.86 (1H, s), 6.80-7.10 (1H, br)

Synthesis Example 3

Synthesis of (E-1)

Under a nitrogen atmosphere, 1.44 kg (12.8 mol) of potassium tert-butoxide was dissolved in 10.4 L of tetrahydrofuran. Thereafter, while keeping the internal temperature at 10° C. or lower, a solution of 2.08 kg (11.2 mol) of the (C-1) dissolved in 2.08 L of tetrahydrofuran was added dropwise to the solution over 1 hour. Subsequently, 1.58 kg (13.4 mol) of dimethyl oxalate was added to the solution, and the obtained mixture was then stirred at 40° C. for 2 hours. Thereafter, 16.0 L of methanol was further added to the reaction solution, followed by concentration, so as to obtain a methanol solution of (D-1). The thus obtained solution was directly used in the subsequent reaction.

$^1$H-NMR (DMSO-d$_6$) δ value: 1.15 (6H, t, J=7.2 Hz), 3.52-3.58 (4H, m), 3.60 (3H, s), 4.75 (1H, s), 7.88 (1H, br)

Under a nitrogen atmosphere, while keeping the internal temperature at 10° C. or lower, 0.979 L (13.2 mol) of trifluoroacetic acid was added dropwise to the obtained methanol solution of (D-1), and 0.815 kg (11.7 mol) of hydroxylamine hydrochloride was then added to the mixture. While stirring, the obtained mixture was heated to reflux for 5 hours. Thereafter, the reaction solution was cooled to room temperature, and methanol was then distilled away under reduced pressure. Thereafter, 10.4 L of ethyl acetate and 8.30 L of a 20.0% sodium chloride aqueous solution were added to the residue. After stirring, a liquid separation operation was performed, and an aqueous layer was then removed. To the remaining organic layer, 8.30 L of a 20.0% sodium chloride aqueous solution and 0.260 kg of sodium bicarbonate were added. After stirring, a liquid separation operation was performed, and an aqueous layer was then removed. To the organic layer, 8.30 L of a 20.0% sodium chloride aqueous solution was added again. After stirring, a liquid separation operation was performed, and an aqueous layer was then removed. The organic layer was concentrated, so as to obtain 3.14 kg (purity: 49.0%) of brown oil (E-1). Yield from the (C-1): 47.9%.

$^1$H-NMR (CDCl$_3$) δ value: 1.32 (6H, t, J=6.8 Hz), 3.50-3.80 (m, 4H), 3.98 (3H, s), 4.93 (1H, s), 5.82 (2H, br), 9.29 (1H, br)

Synthesis Example 4

Synthesis of (F-1)

1.55 kg (5.40 mol) of the (E-1) was dissolved in 3.90 L of acetic acid, and 213 g (1.12 mol) of p-toluenesulfonic acid monohydrate was then added to the solution. The obtained mixture was reacted at an internal temperature of 77° C. to 80° C. for 2 hours. Thereafter, the obtained reaction mixture was cooled to room temperature, and 8.00 L of water was then added to the mixture, followed by stirring for 20 minutes. Thereafter, a precipitate was collected by filtration, and it was then washed with water until the pH of the filtrate became pH 5 or greater. Thereafter, the resultant was dried at 40° C. overnight, so as to obtain 615 g of a light yellow solid (F-1). Yield: 58.4%.

$^1$H-NMR (DMSO-d$_6$) δ value: 3.99 (3H, s), 8.26 (1H, s), 12.75-13.00 (1H, br)

It is to be noted that, since the (F-1) was a solid and had low volatility and low skin irritancy, it could be safely and easily used in the subsequent reaction.

Synthesis Example 5

Synthesis of (G-1)

156 g (0.800 mol) of the (F-1) was mixed with 373 mL (4.00 mol) of phosphorus oxychloride, and 110 g (0.800 mol) of triethylamine hydrochloride was then added to the mixture. The obtained mixture was reacted at an internal temperature of 85° C. for 4 hours. Thereafter, the reaction solution was cooled to room temperature. A mixed solution of 800 mL of toluene and 1600 mL of water was cooled on ice, and the above-obtained reaction mixture was then added to the mixed solution over 1 hour, while keeping an internal temperature at 25° C. to 30° C. The reaction mixture was further stirred at an internal temperature of 22° C. to 23° C. for 1 hour, and it was then left at rest. An aqueous layer was removed, and 800 mL of a saturated saline was added to the organic layer. Thereafter, the reaction mixture was stirred and was then left at rest, and an aqueous layer was removed. This operation was repeatedly performed four times. In the 4$^{th}$ operation, the pH of the aqueous layer was pH 6. Anhydrous sodium sulfate was added to the obtained organic layer, followed by stirring. After the removal of sodium sulfate, the solvent was distilled away under reduced pressure, so as to obtain 152 g of a light brown solid (G-1). Yield: 88.9%.

$^1$H-NMR (CDCl$_3$) δ value: 4.14 (3H, s), 8.65 (1H, s)

It is to be noted that, since the (G-1) was a solid and had low volatility and low skin irritancy, it could be safely and easily used in the subsequent reaction.

Synthesis Example 6

Synthesis of (H-1)

Under a nitrogen atmosphere, a mixed solution of 2.00 g (10.3 mmol) of (F-1) and 40.0 mL of acetonitrile was stirred, and 1.88 mL (15.4 mmol) of 2,2-difluoro-1,3-dimethylimidazolidine was then added dropwise thereto. After completion of the dropwise addition, the obtained mixture was stirred at a temperature of 80 to 90° C. for 3 hours. Thereafter, the reaction solution was concentrated under reduced pressure, and the obtained residue was then separated and purified by silica gel chromatography (eluent: hexane/ethyl acetate=2/1 (volume ratio)). As a result, 0.900 g of a white solid (H-1) was obtained. Yield: 44.4%.

$^1$H-NMR (CDCl$_3$) δ value: 8.53 (1H, d, J=6.6 Hz), 4.14 (3H, s)

$^{19}$F-NMR (CDCl$_3$) δ value: −78.74 (1F, d, J=6.6 Hz)

It is to be noted that, since the (H-1) was a solid and had low volatility and low skin irritancy, it could be safely and easily used in the subsequent reaction.

Synthesis Example 7

Synthesis of (H-1)

1.80 g (31.0 mmol) of potassium fluoride was mixed with 22.0 mL of dimethyl sulfoxide, and 15.0 mL of toluene was then added to the mixture, followed by stirring. Thereafter, toluene was distilled away under reduced pressure at an external temperature of 80° C. at 70 mmHg, and 1.07 g (5.00 mmol) of the (G-1) was added to the residue, followed by a reaction at an internal temperature of 80° C. for 3 hours. Thereafter, the reaction product was cooled to room temperature, and 300 mL of ethyl acetate and 200 mL of water were then added thereto. The reaction mixture was stirred and was then left at rest, and an aqueous layer was removed. This operation was repeatedly performed twice. Subsequently, 50.0 mL of a saturated saline was added to the organic layer, and the obtained mixture was then stirred and left at rest, so as to remove an aqueous layer. The resultant was dried over magnesium sulfate and was then filtrated. The filtrated was concentrated, so as to obtain a mixture of 0.830 g of a brown solid (H-1) and 0.03 g of the (G-1). Yield: 84.0%. (The ingredient ratio in the mixture was calculated based on the integral values of NMR spectra.)

Synthesis Example 8

Synthesis of T-705A 3.00 mL of tetrahydrofuran, 3.00 mL of water and 55.0 mg (1.38 mmol) of sodium hydroxide were added to 200 mg (1.01 mmol) of the (H-1), and while stirring the obtained mixture was heated at 80° C. for 3 hours. Thereafter, the reaction solution was cooled to room temperature, and ion exchange resin DOWEX (registered trademark) 50W×2-200 (H) was added thereto. Thereafter, the resultant was filtrated and concentrated, so as to obtain 126 mg of T-705A in the form of a yellow solid. Yield: 89.7%.

$^1$H-NMR (DMSO-d$_6$) δ value: 8.22 (1H, d, J=8.1 Hz), 13.85 (1H, br)

$^{19}$F-NMR (DMSO-d$_6$) δ value: −94.13 (1H, br)

It is apparent that, according to the method of treating the T-705A with a basic aqueous solution described in Production Example 4 of Patent Document 1 or Production Example 1 of Patent Document 2 or the like, T-705 can be produced using the T-705A synthesized by the method of the present invention.
Further, examples of synthesizing the pyrazino[2,3-d]isoxazole derivative of the present invention and the like will be described in detail below.
[Chem. 23]
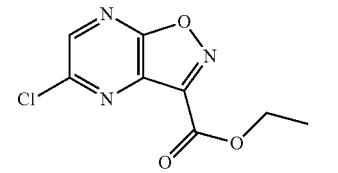
(A-1a)
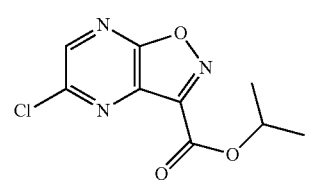
(A-2)
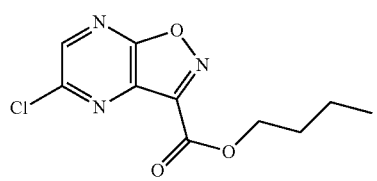
(A-3)
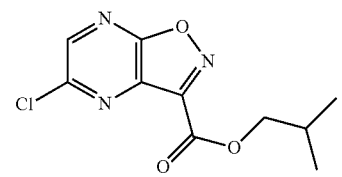
(A-4)
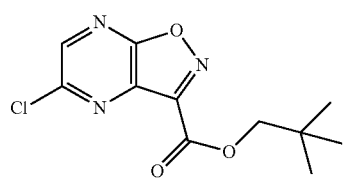
(A-5)
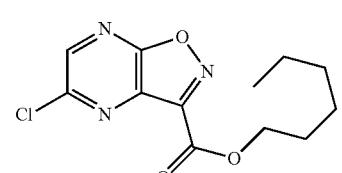
(A-6)
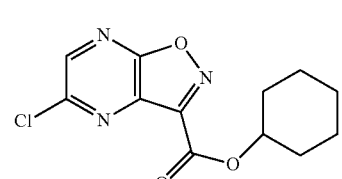
(A-7)
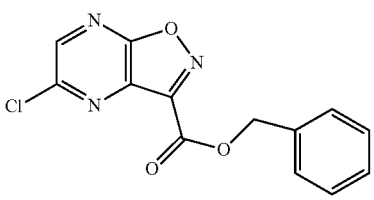
(A-8)
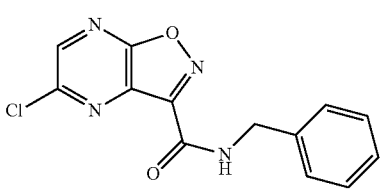
(A-9)
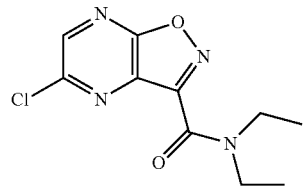
(A-10)
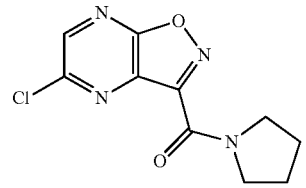
(A-11)
[Chem. 24]
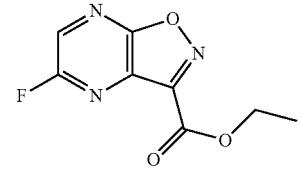
(A-12)
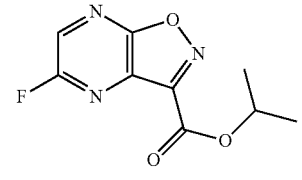
(A-13)
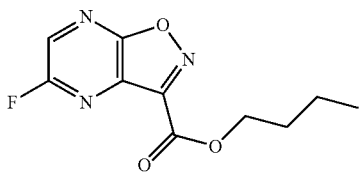
(A-14)
(A-15)

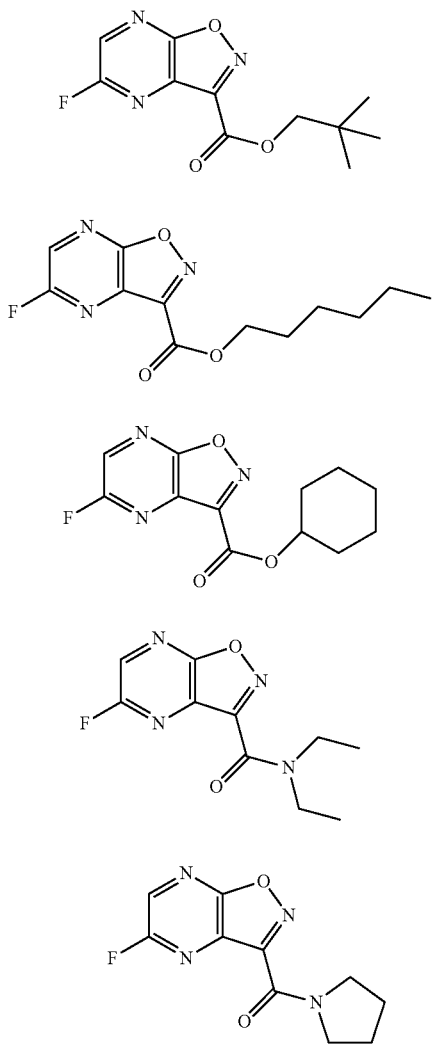

(A-16)
(A-17)
(A-18)
(A-19)
(A-20)

[Chem. 25]

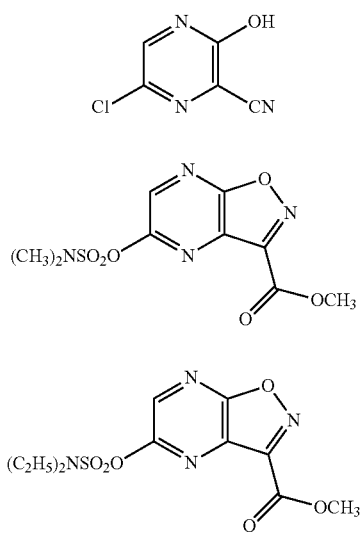

(A-21)
(A-22)
(A-23)

(A-24)
(A-25)
(A-26)

Synthesis Example 9

Synthesis of (A-1a)

10.7 g (50.0 mmol) of the (G-1) was mixed with 50.0 mL of ethyl alcohol, and 17.4 mL (100 mmol) of diisopropylethylamine and 0.610 g (5.00 mmol) of 4-dimethylaminopyridine were then added to the mixture. The obtained mixture was reacted at an internal temperature of 80° C. for 2.5 hours, and it was then cooled to room temperature. The reaction solution was concentrated, and the residue was then subjected to silica gel chromatography (hexane:ethyl acetate=4:1), so as to obtain 7.39 g of a white solid (A-1a). Yield: 64.8%.

$^1$H-NMR (CDCl$_3$) δ value: 8.62 (1H, s), 4.60 (2H, q, J=7.0 Hz), 1.51 (3H, t, J=7.0 Hz)

Synthesis Example 10

Synthesis of (A-2)

42.7 g (0.200 mol) of the (G-1) was mixed with 500 mL of isopropyl alcohol, and 42.0 mL (0.300 mol) of triethylamine was then added to the mixture. The obtained mixture was reacted at an internal temperature of 80° C. for 2 hours, and it was then cooled to room temperature. The reaction solution was concentrated, and the residue was then subjected to silica gel chromatography (hexane:ethyl acetate=4:1), so as to obtain 41.6 g of a white solid (A-2). Yield: 86.0%.

$^1$H-NMR (CDCl$_3$) δ value: 8.63 (1H, s), 5.45 (1H, quint, J=6.0 Hz), 1.49 (6H, s)

Synthesis Example 11

Synthesis of (A-3)

32.0 g (150 mmol) of the (G-1) was mixed with 150 mL of 1-butyl alcohol, and 52.3 mL (300 mmol) of diisopropylethylamine and 1.83 g (15.0 mmol) of 4-dimethylaminopyridine were then added to the mixture. The obtained mixture was reacted at an internal temperature of 90° C. for 2 hours, and it was then cooled to room temperature. The reaction solution was concentrated, and the residue was then subjected to silica gel chromatography (hexane:ethyl acetate=4:1), so as to obtain 25.1 g of a white solid (A-3). Yield: 65.4%.

$^1$H-NMR (CDCl$_3$) δ value: 8.63 (1H, s), 4.55 (2H, t, J=6.8 Hz), 1.81-1.89 (2H, m), 1.47-1.57 (2H, m), 1.00 (3H, t, J=7.2 Hz)

Synthesis Example 12

Synthesis of (A-4)

1.00 g (4.39 mmol) of the (A-1a) was dissolved in 10.0 mL of isobutyl alcohol, and 107 mg (0.878 mmol) of 4-dimethylaminopyridine was then added to the solution. The obtained mixture was stirred under heating at 100° C. for 5 hours. Thereafter, the reaction solution was cooled to room temperature and was then concentrated. The residue was purified by silica gel chromatography (hexane:ethyl acetate=4:1), so as to obtain 0.780 g of (A-4) in the form of light yellow oil. Yield: 69.4%.

$^1$H-NMR (CDCl$_3$) δ value: 1.07 (6H, d, J=6.8 Hz), 2.19 (1H, h, J=6.7 Hz), 4.32 (2H, d, J=6.6 Hz), 8.63 (1H, s)

Synthesis Example 13

Synthesis of (A-5)

1.07 g (5.00 mmol) of the (G-1) was mixed with 5.00 g of neopentyl alcohol, and 1.70 mL (10.0 mmol) of diisopropylethylamine was then added to the mixture. The obtained mixture was reacted at an internal temperature of 100° C. for 5 hours. Thereafter, the reaction solution was cooled to room temperature, and 30.0 mL of ethyl acetate and 20.0 mL of water were then added thereto. The reaction mixture was stirred and was then left at rest, and an aqueous layer was removed. This operation was repeatedly performed twice. The organic layer was concentrated, and the residue was then subjected to silica gel chromatography (hexane:ethyl acetate=4:1), so as to obtain 0.750 g of a white solid (A-5). Yield: 55.6%.

$^1$H-NMR (CDCl$_3$) δ value: 8.63 (1H, d, J=6.6 Hz), 4.23 (2H, s), 1.09 (9H, s)

Synthesis Example 14

Synthesis of (A-6)

2.28 g (10.0 mmol) of the (A-1a) was mixed with 10.0 g of 1-hexyl alcohol, and 3.48 mL (20.0 mmol) of diisopropylethylamine and 0.120 g of 4-dimethylaminopyridine were then added to the mixture. The obtained mixture was reacted at an internal temperature of 80° C. for 3.5 hours. Thereafter, the reaction solution was cooled to room temperature. The reaction solution was concentrated, and the residue was then subjected to silica gel chromatography (hexane:ethyl acetate=4:1), so as to obtain 2.30 g of a white solid (A-6). Yield: 81.0%.

$^1$H-NMR (CDCl$_3$) δ value: 8.63 (1H, s), 4.54 (2H, t, J=6.8 Hz), 1.81-1.90 (2H, m), 1.31-1.53 (6H, m), 0.91 (3H, t, J=7.2 Hz)

Synthesis Example 15

Synthesis of (A-7)

2.14 g (10.0 mmol) of the (G-1) was mixed with 10.0 g of cyclohexyl alcohol, and 2.00 mL (10.0 mmol) of diisopropylethylamine and 0.210 g of 4-dimethylaminopyridine were then added to the mixture. The obtained mixture was reacted at an internal temperature of 100° C. for 1 hour. Thereafter, the reaction solution was cooled to room temperature, and 100 mL of ethyl acetate and 50.0 mL of hydrochloric acid (1 mol/L) were then added thereto. The reaction mixture was stirred and was then left at rest, and an aqueous layer was removed. This operation was repeatedly performed twice. Subsequently, 20.0 mL of a saturated saline was added to the organic layer, and the obtained mixture was then stirred and left at rest, so as to remove an aqueous layer. The resultant was dried over magnesium sulfate and was then filtrated. The filtrate was concentrated, and the residue was then subjected to silica gel chromatography (hexane:ethyl acetate=4:1), so as to obtain 1.30 g of a white solid (A-7). Yield: 46.1%.

$^1$H-NMR (CDCl$_3$) δ value: 8.62 (1H, s), 5.19-5.28 (1H, m), 1.31-2.08 (10H, m)

Synthesis Example 16

Synthesis of (A-8)

2.28 g (10.0 mmol) of the (A-1a) was mixed with 2.08 mL (20.0 mmol) of benzyl alcohol, and 20.0 mL of diisopropylethylamine was then added to the mixture. The obtained mixture was reacted at an internal temperature of 80° C. for 1 hour. Thereafter, the reaction solution was cooled to room temperature. The reaction solution was concentrated, and the residue was then recrystallized (hexane/ethyl acetate), so as to obtain 0.780 g of a white solid (A-8). Yield: 26.9%.

$^1$H-NMR (CDCl$_3$) δ value: 8.62 (1H, s), 7.32-7.57 (5H, m), 5.57 (2H, s)

Synthesis Example 17

Synthesis of (A-9)

0.430 g (2.00 mmol) of the (G-1) was mixed with 4.00 mL of ethyl alcohol, and 0.220 mL (2.00 mmol) of benzyl alcohol was then added to the mixture. The obtained mixture was reacted at room temperature for 1 hour. The reaction solution was concentrated, and the residue was then subjected to silica gel chromatography (hexane:ethyl acetate=4:1), so as to obtain 0.490 g of a yellow solid (A-9). Yield: 84.8%.

$^1$H-NMR (CDCl$_3$) δ value: 8.64 (1H, s), 7.31-7.42 (5H, m), 4.77 (2H, d, J=6.0 Hz)

Synthesis Example 18

Synthesis of (A-10)

6.41 g (30.0 mmol) of the (G-1) was mixed with 16.0 mL (150 mmol) of diethylamine, and the obtained mixture was then reacted at 50° C. for 45 minutes. The reaction solution was concentrated, and the residue was then subjected to silica gel chromatography (hexane:ethyl acetate=4:1), so as to obtain 6.33 g of a yellow solid (A-10). Yield: 82.7%.

$^1$H-NMR (CDCl$_3$) δ value: 8.60 (1H, s), 3.67 (2H, t, J=7.2 Hz), 3.47 (2H, t, J=7.2 Hz), 1.34 (3H, t, J=7.2 Hz), 1.26 (3H, t, J=7.2 Hz)

Synthesis Example 19

Synthesis of (A-11)

2.14 g (10.0 mmol) of the (G-1) was mixed with 15.0 mL of methyl alcohol, and 0.860 mL (10.5 mmol) of pyrrolidine was then added to the mixture. The obtained mixture was reacted at room temperature for 40 minutes. Thereafter, the reaction solution was concentrated, and the residue was then subjected to silica gel chromatography (hexane:ethyl acetate=4:1), so as to obtain 2.27 g of a yellow solid (A-11). Yield: 89.7%.

$^1$H-NMR (CDCl$_3$) δ value: 8.61 (1H, s), 3.72-3.81 (4H, m), 1.98-2.05 (4H, m)

Synthesis Example 20

Synthesis of (A-12)

0.630 g (10.8 mmol) of potassium fluoride was mixed with 14.4 mL of dimethyl sulfoxide, and the solvent was then distilled away under reduced pressure at an external temperature of 80° C. at 3 to 5 hPa. Thereafter, 15.0 mL of dry dimethyl sulfoxide and 0.820 g (3.60 mmol) of the (A-1a) were added to the residue, and the obtained mixture was then reacted at an internal temperature of 90° C. for 4 hours. According to high performance liquid chromatographic analysis, the production rate was found to be 97.0%. (As an internal standard, diphenyl ether was used.)

Synthesis Example 21

Synthesis of (A-13)

3.50 g (60.0 mmol) of potassium fluoride was mixed with 250 mL of dimethyl sulfoxide, and the solvent was then distilled away under reduced pressure at an external temperature of 130° C. at 21 mmHg. Thereafter, 80.0 mL of dry dimethyl sulfoxide and 4.83 g (20.0 mmol) of the (A-2) were added to the residue, and the obtained mixture was then reacted at an internal temperature of 90° C. for 4 hours. The reaction solution was cooled to room temperature, and 100 mL of toluene and 100 mL of water were added thereto. The reaction mixture was stirred and was then left at rest, and an aqueous layer was removed. This operation was repeatedly performed twice. Subsequently, 100 mL of a saturated saline was added to the obtained organic layer, and the obtained mixture was then stirred and left at rest, so as to remove an aqueous layer. The resultant was dried over magnesium sulfate and was then filtrated. The filtrate was concentrated, so as to obtain 3.97 g of a solid (A-13). Yield: 88.2%.

$^1$H-NMR (CDCl$_3$) δ value: 8.50 (1H, d, J=6.4 Hz), 5.46 (1H, quintet, J=6.4 Hz), 1.49 (6H, d, J=6.4 Hz)

$^{19}$F-NMR (CDCl$_3$) δ value: −79.16 (1F, d, J=6.4 Hz)

Synthesis Example 22

Synthesis of (A-14)

0.360 g (6.20 mmol) of potassium fluoride was mixed with 8.00 mL of dimethyl sulfoxide, and 14.0 mL of toluene was added to the mixture, followed by stirring. Thereafter, toluene was distilled away under reduced pressure at an external temperature of 80° C. at 70 mmHg. Subsequently, 0.510 g (2.00 mmol) of the (A-3) was added to the residue, and the obtained mixture was then reacted at an internal temperature of 80° C. for 2 hours and at an internal temperature of 90° C. for 1.5 hours. Thereafter, the reaction solution was cooled to room temperature, and 30.0 mL of toluene and 20.0 mL of water were added thereto. The reaction mixture was stirred and was then left at rest, and an aqueous layer was removed. This operation was repeatedly performed three times. Subsequently, 20.0 mL of a saturated saline was added to the organic layer, and the obtained mixture was then stirred and left at rest, so as to remove an aqueous layer. The resultant was dried over magnesium sulfate and was then filtrated. The filtrate was concentrated, and the residue was then subjected to silica gel chromatography (hexane:ethyl acetate=4:1), so as to obtain 0.400 g of a white solid (A-14). Yield: 83.7%.

$^1$H-NMR (CDCl$_3$) δ value: 8.51 (1H, d, J=6.4 Hz), 4.54 (2H, t, J=6.8 Hz), 1.81-1.89 (2H, m), 1.47-1.57 (2H, m), 1.00 (3H, t, J=7.2 Hz)

$^{19}$F-NMR (CDCl$_3$) δ value: −79.02 (1F, d, J=6.4 Hz)

Synthesis Example 23

Synthesis of (A-15)

Under a nitrogen atmosphere, 4.68 mL of dimethyl sulfoxide and 10.0 mL of toluene were added to 203 mg (3.51 mmol) of potassium fluoride, and the obtained mixture was then heated to 70° C. Thereafter, toluene was distilled away under reduced pressure. Further, 0.300 g (1.17 mmol) of the (A-4) was added to the residue, and while stirring, the obtained mixture was reacted at 80° C. for 2 hours. As a result of the HPLC analysis of the reaction solution, the production rate was found to be 84.0%. (As an internal standard, diphenyl ether was used.)

Synthesis Example 24

Synthesis of (A-16)

0.190 g of a white solid (A-16) was obtained from 0.230 g (4.00 mmol) of potassium fluoride, 6.00 mL of dimethyl sulfoxide and 0.400 g (1.50 mmol) of the (A-5) by the same operations as those applied in Synthesis Example 22. Yield: 50.1%.

$^1$H-NMR (CDCl$_3$) δ value: 8.51 (1H, d, J=6.6 Hz), 4.22 (2H, s), 1.09 (9H, s)

$^{19}$F-NMR (CDCl$_3$) δ value: −79.11 (1F, d, J=6.6 Hz)

Synthesis Example 25

Synthesis of (A-17)

0.620 g (10.7 mmol) of potassium fluoride was mixed with 14.4 mL of dimethyl sulfoxide, and 14.0 mL of toluene was then added to the mixture, followed by stirring. Thereafter, toluene was distilled away under reduced pressure at an external temperature of 80° C. at 70 mmHg. 0.510 g of the (A-6) was added to the residue, and the obtained mixture was then reacted at an internal temperature of 80° C. for 2 hours, and at an internal temperature of 90° C. for 2 hours. According to high performance liquid chromatographic analysis, the production rate was found to be 89.0%. (As an internal standard, diphenyl ether was used.)

Synthesis Example 26

Synthesis of (A-18)

0.310 g of a white solid (A-18) was obtained from 0.470 g (8.10 mmol) of potassium fluoride, 11.0 mL of dimethyl sulfoxide and 0.760 g (2.70 mmol) of the (A-7) by the same operations as those applied in Synthesis Example 22. Yield: 43.4%.

$^1$H-NMR (CDCl$_3$) δ value: 8.49 (1H, d, J=6.6 Hz), 5.20-5.27 (1H, m), 1.99-2.07 (2H, m), 1.33-1.90 (8H, m)

$^{19}$F-NMR (CDCl$_3$) δ value: −79.21 (1F, d, J=6.6 Hz)

Synthesis Example 27

Synthesis of (A-19)

0.590 g (10.0 mmol) of potassium fluoride, 12.0 mL of dimethyl sulfoxide and 0.760 g (3.00 mmol) of the (A-10) were reacted at 80° C. for 4 hours by the same operations as those applied in Synthesis Example 25. As a result, the production rate was found to be 65.0%.

Synthesis Example 28

Synthesis of (A-20)

0.520 g (9.00 mmol) of potassium fluoride, 12.0 mL of dimethyl sulfoxide and 0.76 g (3.00 mmol) of the (A-11) were reacted at 80° C. for 4 hours by the same operations as those applied in Synthesis Example 25. As a result, the production rate was found to be 81.0%.

Synthesis Example 29

Synthesis of (A-21)

1.00 mL of tetrahydrofuran, 1.00 mL of water and 20.0 mg (0.491 mmol) of sodium hydroxide were added to 100 mg (0.468 mmol) of the (G-1), and while stirring, the obtained mixture was heated at 80° C. for 1 hour. Thereafter, the reaction solution was cooled to room temperature, and ion exchange resin DOWEX (registered trademark) 50W×2-200 (H) was added thereto. Thereafter, the resultant was filtrated and concentrated, so as to obtain 70.0 mg of (A-21) in the form of a yellow solid. Yield: 95.9%.

$^1$H-NMR (DMSO-$d_6$) δ value: 8.44 (1H, s), 13.85 (1H, br)

Synthesis Example 30

Synthesis of T-705A 2.00 mL of toluene, 1.00 mL of water and 0.224 g (2.66 mmol) of sodium bicarbonate were added to 0.500 g (2.22 mmol) of the (A-15), and while stirring, the obtained mixture was reacted at 80° C. for 3 hours, and at 100° C. for 5 hours. As a result of the high performance liquid chromatographic analysis of the reaction solution, the production rate was found to be 92.0%.

Synthesis Example 31

Synthesis of (A-22)

A mixed solution of 1.36 g (7.00 mmol) of the (F-1), 20.0 mL of acetonitrile and 1.49 mL (9.00 mmol) of diisopropylethylamine was cooled on ice, and 0.860 mL (8.00 mmol) of dimethylcarbamic acid chloride was then added to the solution. The obtained mixture was reacted at room temperature for 1 hour. Thereafter, 100 mL of ethyl acetate and 100 mL of water were added to the reaction solution. The reaction mixture was stirred and was then left at rest, and an aqueous layer was removed. This operation was repeatedly performed twice. Subsequently, the organic layer was dried over magnesium sulfate and was then concentrated. The residue was then subjected to silica gel chromatography (hexane:ethyl acetate=4:1), so as to obtain 0.740 g of a white solid (A-22). Yield: 35.1%.

$^1$H-NMR (CDCl$_3$) δ value: 8.57 (1H, s), 4.10 (3H, s), 3.17 (6H, s)

Synthesis Example 32

Synthesis of (A-23)

A mixed solution of 6.66 g (34.0 mmol) of the (F-1), 50.0 mL of acetonitrile and 6.80 mL (41.0 mmol) of diisopropylethylamine was cooled on ice, and 5.10 mL (41.0 mmol) of dimethylcarbamic acid chloride and 0.370 g (3.00 mmol) of 4-dimethylaminopyridine were then added to the solution. The obtained mixture was reacted at room temperature overnight. Thereafter, the reaction solution was concentrated, and 100 mL of ethyl acetate and 100 mL of diluted hydrochloric acid (1 mol/L) were then added to the concentrate. Then, the reaction mixture was stirred and was then left at rest, and an aqueous layer was removed. This operation was repeatedly performed twice. Subsequently, the organic layer was dried over magnesium sulfate and was then concentrated. The residue was then subjected to silica gel chromatography (hexane:ethyl acetate=4:1), so as to obtain 9.97 g of a yellow liquid (A-23). Yield: 88.4%.

$^1$H-NMR (CDCl$_3$) δ value: 8.56 (1H, s), 4.11 (3H, s), 3.59 (4H, q, J=7.2 Hz), 1.31 (6H, t, J=7.2 Hz)

Synthesis Example 33

Synthesis of (A-24)

1.65 g (5.00 mmol) of the (A-23) was mixed with 5.00 mL of 1-butyl alcohol, and 1.70 mL (10.0 mmol) of diisopropylethylamine was then added to the mixture. The obtained mixture was reacted at an internal temperature of 80° C. for 2 hours. Thereafter, the reaction solution was cooled to room temperature. The reaction solution was concentrated, and the residue was then subjected to silica gel chromatography (hexane:ethyl acetate=4:1), so as to obtain 1.47 g of a yellow liquid (A-24). Yield: 79.0%.

$^1$H-NMR (CDCl$_3$) δ value: 8.55 (1H, s), 4.52 (2H, t, J=6.8 Hz), 3.57 (4H, q, J=7.2 Hz), 1.80-1.88 (2H, m), 1.48-1.57 (2H, m), 1.30 (6H, t, J=7.2 Hz), 1.00 (3H, t, J=7.2 Hz)

Synthesis Example 34

Synthesis of (A-25)

10.0 mL of tetrahydrofuran, 10.0 mL of water and 0.270 g (6.75 mmol) of sodium hydroxide were added to 1.51 g (5.00 mmol) of the (A-22), and while stirring, the obtained mixture was heated at 80° C. for 40 minutes. Thereafter, the reaction solution was cooled to room temperature, and ion exchange resin DOWEX (registered trademark) 50W×2-200 (H) was added thereto. The resultant was filtrated and concentrated, so as to obtain 0.610 g of (A-25) in the form of a yellow solid. Yield: 50.0%.

$^1$H-NMR (DMSO-$d_6$) δ value: 8.04 (1H, s), 2.88 (3H, s)

Synthesis Example 35

Synthesis of (A-21)

2.00 mL of toluene, 1.00 mL of water and 0.340 g (4.00 mmol) of sodium bicarbonate were added to 0.510 g (2.00 mmol) of the (A-10), and while stirring, the obtained mixture was reacted at 100° C. for 2 hours. As a result of the high performance liquid chromatographic analysis of the reaction solution, the production rate was found to be 13.0%.

Synthesis Example 36

Synthesis of T-705A 0.750 mL of N,N-dimethylformamide, 0.120 mL of water and 114 mg (1.16 mmol) of potassium acetate were added to 185 mg (0.773 mmol) of the (A-14). While stirring, the obtained mixture was heated at 80° C. for 3 hours, and it was then cooled to room temperature. As a result of the HPLC analysis of the reaction mixture, the production rate was found to be 57.0%.

Synthesis Example 37

Synthesis of T-705A 2.00 mL of tetrahydrofuran, 1.00 mL of water and 37.0 mg (0.930 mmol) of sodium hydroxide were added to 185 mg (0.773 mmol) of the (A-14). While stirring, the obtained mixture was heated at 80° C. for 1 hour, and it was then cooled to room temperature. As a result of the HPLC analysis of the reaction mixture, the production rate was found to be 94.9%.

Synthesis Example 38

Synthesis of T-705A 2.00 mL of isopropyl alcohol, 1.00 mL of water and 37.0 mg (0.930 mmol) of sodium hydroxide were added to 185 mg (0.773 mmol) of the (A-14). While stirring, the obtained mixture was heated at 80° C. for 1 hour, and it was then cooled to room temperature. As a result of the HPLC analysis of the reaction mixture, the production rate was found to be 85.6%.

Synthesis Example 39

Synthesis of (T-705A)

Under a nitrogen atmosphere, 10.0 mL of dimethyl sulfoxide and 15.0 mL of N,N-dimethylformamide were added to 460 mg (7.91 mmol) of potassium fluoride, and N,N-dimethylformamide was distilled away. Further, 0.460 g (2.61 mmol) of the (A-22) was added thereto, and while starring, the obtained mixture was reacted at 80° C. for 3 hours. The reaction solution was cooled to room temperature, and 50.0 mL of ethyl acetate and 30.0 mL of water were added thereto. The reaction mixture was stirred and was then left at rest. After liquid separation, the obtained organic layer was washed with 30 mL of water, and then with 30 mL of saturated saline, and the solvent was distilled away by evaporator. 2.0 mL of dimethyl sulfoxide, 1.0 mL of water and 0.120 g (3.00 mmol) of sodium hydroxide were added to the residue, and while starring, the resultant mixture was reacted at 80° C. for 3 hours. The reaction solution was cooled to room temperature, and 0.48 mL (2.41 mmol) of dicyclohexylamine was added thereto. After the pH of the solution was adjusted to be pH=9 by concentrated hydrochloric acid, 2.0 mL of acetone and 3.0 mL of water were added thereto. The precipitated crystal was filtered, so as to obtain 0.25 g of dicyclohexylamine salt of T-705A as a light brown solid.

Synthesis Example 40

Synthesis of (A-26)

5.00 g (23.4 mmol) of the (G-1) was mixed with 23.0 mL of 1-propanol, and thereafter, 8.00 mL (46.8 mmol) of diisopropylethylamine and 0.250 g (2.00 mmol) of 4-dimethylaminopyridine were added to the mixture. The obtained mixture was reacted at 80° C. for 70 minutes, and at 90° C. for 110 minutes. Thereafter, the reaction solution was concentrated, and the residue was then subjected to silica gel chromatography, so as to obtain 3.50 g of a light yellow solid (A-26). Yield: 61.8%.

$^1$H-NMR (CDCl$_3$) δ value: 8.64 (1H, s), 4.51 (2H, q, J=6.8 Hz), 1.85-1.94 (2H, m), 1.08 (3H, t, J=7.2 Hz)

Since the compounds (A-1a) to (A-20), (A-22) to (A-24), and (A-26) had low volatility and low skin irritancy, they could be handled safely and easily.

[Chem.26]

(A-27), (A-28), (A-29), (A-30), (A-31), (A-32)

Synthesis Example 41

Synthesis of (A-27)

Under a nitrogen atmosphere, 54 g (0.377 mol) of ethyl-(Z)-4-amino-4-oxo-2-butenoate was dissolved in 300 mL of ethanol, and while keeping the internal temperature at 15 to 25° C., 26.2 g (0.396 mol) of a 50% hydroxylamine aqueous solution was added dropwise to the solution. The obtained mixture was stirred at 20° C. for 4.5 hours, and the reaction solution was then cooled to −20° C. The precipitated solid was filtrated. The thus obtained solid was washed with 50.0 mL of cooled ethyl acetate, so as to obtain 42.4 g of a white solid (A-27). Yield: 63.8%.

$^1$H-NMR (DMSO-$d_6$) δ value: 1.18 (3H, t, J=7.2 Hz), 2.40 (1H, dd, J=7.6, 15.6 Hz), 2.59 (1H, dd, J=6.0, 16.0 Hz), 3.63 (1H, dd, J=6.0, 7.6 Hz), 4.05 (2H, q, J=6.8 Hz), 5.80 (1H, br), 7.12 (1H, br), 7.31 (1H, br), 7.51 (1H, br)

Synthesis Example 42

Synthesis of (A-29)

56.0 g (0.386 mol) of a 40% glyoxal aqueous solution, 125 mL of tetrahydrofuran, 125 mL of water and 13.3 g (0.0955 mol) of potassium carbonate were mixed, and the obtained mixture was then cooled to 12° C. Then, 33.7 g (0.191 mol) of the (A-27) was added to the reaction solution, and the obtained mixture was then stirred at 20° C. for 3 hours. Thereafter, 11.6 g of acetic acid was added to the reaction solution, and the obtained mixture was then concentrated to 80.0 g. 30.0 mL of a saturated saline was added to the concentrate, and the obtained mixture was then stirred. The precipitated solid was filtrated, and the filtrate was washed with 30 mL of a saturated saline and then dried, so as to obtain 14.0 g of a light pink solid (A-29). Yield: 36.7%.

$^1$H-NMR (DMSO-$d_6$) δ value: 1.16 (3H, t, J=6.8 Hz), 3.69 (2H, s), 4.06 (2H, q, J=7.2 Hz), 7.24 (1H, d, J=6.0 Hz), 7.54 (1H, d, J=5.6 Hz), 12.3 (1H, br)

Synthesis Example 43

Synthesis of (A-31)

A solution prepared by adding 1.60 mL (22.5 mmol) of acetyl chloride to 30.0 mL of ethanol was added to a mixture of 5.00 g (0.0252 mol) of the (A-29) and 65.0 mL of ethanol, and the thus obtained mixture was then stirred. Thereafter, 3.70 mL (27.5 mmol) of isoamyl nitrite was added to the reaction solution, and the obtained mixture was then stirred at room temperature for 4 hours. Thereafter, 0.500 mL (3.72 mmol) of isoamyl nitrite was added to the reaction solution, and the obtained mixture was further stirred at room temperature for 3.5 hours. To this reaction solution, a solution prepared by adding 0.500 mL (7.04 mmol) of acetyl chloride to 5.00 mL of ethanol, and 0.500 mL (3.72 mmol) of isoamyl nitrite, were added, and the thus obtained mixture was left overnight. Subsequently, a solution prepared by adding 1.60 mL (22.5 mmol) of acetyl chloride to 20.0 mL of ethanol, and 1.50 mL (11.1 mmol) of isoamyl nitrite, were added to the reaction solution, and the thus obtained mixture was then stirred at 35° C. Thereafter, the solvent was concentrated under reduced pressure. Acetonitrile was added to the resultant, and the obtained mixture was then cooled on ice. The precipitated solid was filtrated, so as to obtain 4.10 g of a white solid (A-31). Yield: 71.5%.

$^1$H-NMR (DMSO-$d_6$) δ value: 13.0 (1H, br), 1 2.4 (1H, br), 7.66 (1H, d, J=6.0 Hz), 7.29 (1H, d, J=6.0 Hz), 4.20 (2H, q, J=7.0 Hz), 1.21 (3H, t, J=7.0 Hz)

Synthesis Example 44

Synthesis of (A-1a)

12.0 mL of toluene and 12.0 mL of dimethylformamide were cooled on ice, and 4.60 mL (49.3 mmol) of phosphorus oxychloride was then added thereto. Thereafter, 2.27 g (10.0 mmol) of the (A-31) was added to the mixture, and the thus obtained mixture was then stirred at 70° C. for 4.5 hours. Thereafter, the reaction solution was cooled to room temperature, and ethyl acetate and water were then added thereto. The obtained mixture was stirred and was then left at rest. Thereafter, an aqueous layer was removed, and the organic layer was concentrated under reduced pressure. The obtained residue was separated by silica gel chromatography (eluent: hexane/ethyl acetate=9/1). As a result, 1.60 g of a white solid (A-1a) was obtained. Yield: 70.3%.

Synthesis Example 45

Synthesis of isopropyl-(Z)-4-amino-4-oxo-2-butenoate 196 g (2.00 mol) of maleic anhydride was dissolved in 123 g (2.05 mol) of 2-propanol and 800 mL of ethyl acetate. Thereafter, 300 mL (2.15 mol) of triethylamine was added dropwise to the solution at an internal temperature of 10° C. or lower over 1.5 hours, and the obtained mixture was then stirred for 1 hour. Thereafter, 193 mL (2.03 mol) of ethyl chloroformate was added dropwise to the reaction mixture at an internal temperature of −5° C. or lower over 2 hours. After the mixture had been stirred for 30 minutes, the obtained reaction mixture was added dropwise to an aqueous solution containing 300 mL (2.16 mol) of 28% ammonia water and 250 g of ice. The obtained reaction mixture was left at room temperature overnight. Thereafter, 400 mL of ethyl acetate was added to reaction product, followed by stirring. Thereafter a liquid separation operation was performed on the reaction solution, so as to remove an aqueous layer. This operation was repeated three times. The obtained organic layers were gathered and were then concentrated. Recrystallized from hexane/ethyl acetate was performed, so as to obtain 50.5 g of isopropyl-(Z)-4-amino-4-oxo-2-butenoate in the form of a white solid. Yield: 16.1%.

$^1$H-NMR (DMSO-$d_6$) δ value: 1.20 (6H, d, J=6.0 Hz), 4.94 (1H, sep, J=6.4 Hz), 6.15 (1H, d, J=11.6 Hz), 6.26 (1H, d, J=12.0 Hz), 7.18 (1H, br), 7.57 (1H, br)

Synthesis Example 46

Synthesis of (A-28)

13.9 g (0.210 mol) of a 50% hydroxylamine aqueous solution was dissolved in 200 mL of 2-propanol. While keeping the internal temperature at 3.5 to 6° C. in an ice bath, 31.4 g (0.200 mol) of isopropyl-(Z)-4-amino-4-oxo-2-butenoate was added to the solution over 15 minutes, and 20.0 mL of 2-propanol was further added thereto. The obtained reaction solution was stirred at room temperature for 3 hours, and it was then left at rest in a refrigerator. The precipitated solid was collected by filtration, and it was then washed with cold 2-propanol. The resultant was dried under reduced pressure at room temperature, so as to obtain 22.3 g of a white solid (A-28). Yield: 58.6%.

$^1$H-NMR (DMSO-$d_6$) δ value: 1.18 (6H, d, J=6.4 Hz), 2.36 (1H, dd, J=8.0, 16.0 Hz), 2.55 (1H, dd, J=6.0, 16.0 Hz), 3.61 (1H, t, J=6.8 Hz), 4.87 (1H, sep, J=6.4, 6.4 Hz), 5.70-5.90 (1H, br), 7.00-7.18 (1H, br), 7.20-7.35 (1H, br), 7.46 (1H, s)

Synthesis Example 47

Synthesis of (A-28)

9.43 g (60.0 mmol) of isopropyl-(E)-4-amino-4-oxo-2-butenoate was dissolved in 28.3 mL of tetrahydrofuran, and the obtained solution was then heated in a water bath that was set at 42° C. 4.16 g (63.0 mmol) of a 50% hydroxylamine aqueous solution was added dropwise to the solution over 20 minutes, and the obtained reaction solution was then stirred at 42° C. for 1 hour. Thereafter, 9.40 mL of water was added to the reaction solution, and tetrahydrofuran was then distilled away under reduced pressure. It was confirmed by $^1$H-NMR that the raw material disappeared from the obtained solution and (A-28) was contained therein.

$^1$H-NMR (D$_2$O) δ value: 1.26 (6H, d, J=6.4 Hz), 2.68 (1H, dd, J=6.8, 16.4 Hz), 2.77 (1H, dd, J=7.2, 16.0 Hz), 3.96 (1H, t, J=6.8 Hz), 5.01 (1H, sep, J=6.4, 6.4 Hz)

Synthesis Example 48

Synthesis of (A-30)

3.72 g (25.0 mmol) of a 39% glyoxal aqueous solution was dissolved in 30.0 mL of 2-propanol. The internal temperature was set at 41° C. in a hot water bath. Thereafter, 2.38 g (12.5 mmol) of the (A-28) was dissolved in 2.00 mL of water and 4.00 mL of 2-propanol, and the obtained solution was then added dropwise to the above-obtained solution. During this operation, together with the above-described solution, a 1 mol/L sodium carbonate aqueous solution was also added dropwise thereto, so that the pH of the reaction solution could be maintained at pH 8.9 to 9.1. The obtained reaction mixture was reacted at an internal temperature of 41° C. for 2 hours. The internal temperature was decreased to 20° C., and acetic acid was added to the reaction product, so as to adjust the pH to be pH 6.0. The solvent was distilled away under reduced pressure, and a saturated saline was then added to the residue. The generated solid was collected by filtration, and it was then washed with a cold saturated saline, followed by drying, so as to obtain 2.89 g of a light brown solid (A-30). Yield: 62.3% (purity: 57.2%).

$^1$H-NMR (DMSO-d$_6$) δ value: 1.17 (6H, d, J=6.0 Hz), 3.66 (2H, s), 4.87 (1H, sep, J=6.4, 6.4 Hz), 7.24 (1H, d, J=5.6 Hz), 7.53 (1H, d, J=5.6 Hz), 12.00-12.50 (1H, br)

Synthesis Example 49

Synthesis of (A-30)

12.22 g (77.8 mmol) of isopropyl-(E)-4-amino-4-oxo-2-butenoate was dissolved in 19.8 mL of THF, and the obtained solution was cooled to 15 to 20° C. in a water bath. 5.14 g (77.8 mmol) of a 50% hydroxylamine aqueous solution was added dropwise to the solution over 1 minute, and the obtained reaction solution was then stirred at 27 to 30° C. for 3 hours. It was confirmed by $^1$H-NMR that the raw material disappeared from the obtained solution and (A-28) was contained therein.

0.118 g of sodium bicarbonate was dissolved in 18.3 mL of water. 20.31 g (140.0 mmol) of a 40% glyoxal aqueous solution and the aforementioned THF solution of the (A-28) were added dropwise thereto over 60 minutes. During this operation, together with the above-described solution, a 50% sodium hydroxide aqueous solution was also added dropwise thereto, so that the pH of the reaction solution could be maintained at pH 8.2 to 8.4 (three solutions were simultaneously added dropwise). The obtained reaction mixture was reacted at an internal temperature of 50° C. for 1 hour. During this operation, a 50% sodium hydroxide aqueous solution was added dropwise thereto, so that the pH of the reaction solution could be maintained at pH 8.4. THF was distilled away under reduced pressure, and 5.0 g of saline was then added to the residue. Concentrated hydrochloric acid is added at an internal temperature of 40 to 50° C. so as to adjust the pH to be pH3.0. The solution was cooled to 5° C. over 1 hour, and filtered. The solid on a mesh was washed twice with 10 mL of water of 5° C. or lower followed by drying, so as to obtain 10.80 g of a light brown solid (A-30) (purity: 90%). Yield from A-28: 58.9%

Synthesis Example 50

Synthesis of (A-32)

Under a nitrogen atmosphere, 20.0 mL of isopropyl alcohol was added to 4.60 g (21.7 mmol) of the (A-30), and while stirring, the obtained mixture was cooled to 5° C. Further, 2.86 mL (40.3 mmol) of acetyl chloride was added dropwise to the reaction solution, while keeping the internal temperature at 10° C. or lower. The temperature of the reaction mixture was increased to 40° C., and 5.41 mL (40.3 mmol) of isoamyl nitrite was then added dropwise thereto. After completion of the dropwise addition, the obtained mixture was stirred at 25° C. for 1.5 hours, and it was then cooled to −10° C. The precipitated solid was filtrated, and it was then washed with 5.00 mL of toluene twice. The resultant was dried, so as to obtain 4.59 g of a light yellow solid (A-32). Yield: 87.9%.

$^1$H-NMR (DMSO-d$_6$) δ value: 1.22 (6H, d, J=6.0 Hz), 5.01 (1H, sep, J=6.4 Hz), 7.28 (1H, d, J=5.6 Hz), 7.65 (1H, d, J=5.6 Hz), 12.4 (1H, br), 13.0 (1H, br)

Synthesis Example 51

Synthesis of (A-2)

Under a nitrogen atmosphere, while stirring a mixed solution of 25.0 g (0.104 mol) of the (A-32), 62.5 mL of N,N-dimethylformamide and 62.5 mL of toluene, the internal temperature was kept at 15° C. or lower, and 47.3 mL (0.510 mol) of phosphorus oxychloride was added dropwise to the mixed solution. After completion of the dropwise addition, the temperature of the reaction solution was increased to 70° C., and the reaction solution was then stirred for 7 hours. Thereafter, the reaction solution was cooled to room temperature, and then, the thus obtained reaction mixture was slowly added dropwise to a mixed solution of 62.5 mL of toluene and 300 mL of a 10% saline at an internal temperature of 10° C. or lower. After completion of a liquid separation operation, the organic layer was washed with 100 mL of a 10% saline twice, and then with 100 mL of a 10% sodium bicarbonate solution and with 100 mL of a 10% saline. This organic layer was concentrated, and 7.50 mL of isopropyl alcohol and 150 mL of hexane were then added to the residue. The precipitated solid was filtrated, and it was then washed twice with 15.0 mL of a mixed solvent of isopropyl alcohol/hexane=5/95 (volume ratio), so as to obtain 12.6 g of a light pink solid (A-2) (purity: 98.3%). Yield: 49.3%.

Synthesis Example 52

Synthesis of (A-13)

0.219 g (2.00 mmol) of tetramethylammonium chloride, 2.32 g (40.0 mmol) of potassium fluoride, 9.70 mL of dry dimethyl sulfoxide and 38.6 mL of dry toluene were mixed. Thereafter, toluene was distilled away under reduced pressure at an external temperature of 120° C. After the mixture was cooled to room temperature, 0.203 g (1.00 mmol) of 2,4- dinitrochlorobenzene and 4.83 g (20.0 mmol) of the (A-2) were added to the reaction solution, and the obtained mixture was then reacted at an internal temperature of 90° C. for 2 hours. After the mixture was cooled to room temperature, 0.180 mL of water was added to the reaction solution, and the obtained mixture was then stirred for 2.5 hours. Thereafter, 0.180 mL of water was further added to the reaction solution, and the obtained mixture was then stirred for 1 hour. Thereafter, 14.5 mL of toluene and 14.2 mL of water were added to the reaction solution, and the obtained mixture was stirred and was then left at rest, so as to remove an aqueous layer. Then, 14.5 mL of a saturated sodium bicarbonate solution was added to the organic layer, and the obtained mixture was stirred and was then left at rest, so as to remove an aqueous layer. As a result, a light yellow solution of (A-13) was obtained, and no black tar component was found. This solution was directly used in the subsequent process.

Synthesis Example 53

Synthesis of dicyclohexylamine salt of T-705A 14.5 mL of water and 3.36 g (40.0 mmol) of sodium bicarbonate were added to the solution of the (A-13) obtained in the above-described Synthesis Example 52, and the obtained mixture was then reacted at an external temperature of 100° C. for 4 hours. Thereafter, an organic layer was removed, and 3.43 mL (60.0 mmol) of acetic acid was then added to the aqueous layer. The obtained mixture was refluxed under reduced pressure at an external temperature of 70° C. at 100 mmHg for 1.5 hours. The mixture was cooled to room temperature, and thereafter, 5.00 mL of water, 9.60 L of acetone, and 3.30 mL of 28% ammonia water were added to the reaction solution. Then, 3.78 mL (19.0 mmol) of dicyclohexylamine was added dropwise to the mixed solution over 10 minutes, and the obtained mixture was then stirred at room temperature for 1 hour. Thereafter, 9.60 mL of water was added to the reaction solution, the obtained mixture was then stirred at an internal temperature of 5° C. for 1 hour, and a solid was then filtered. The solid on a Nutsche was successively washed with 10.0 mL of water, a mixed solution of 5.00 mL of acetone and 5.00 mL of water, and 10.0 mL of acetone of 10° C. or lower. The resultant was dried, so as to obtain 5.37 g of dicyclohexylamine salt of T-705A in the form of a light brown solid. Yield: 83.0%; and HPLC purity: 99.0%.

Synthesis Example 54

Synthesis of T-705

10.0 mL of toluene and a sodium hydroxide aqueous solution (prepared by dissolving 0.656 g of sodium hydroxide in 20.0 mL of water) were added to 5.00 g (15.6 mmol) of dicyclohexylamine salt of T-705A, and the obtained mixture was then stirred at room temperature for 30 minutes. The reaction solution was left at rest for 10 minutes, and an upper layer was then removed. 10.0 mL of toluene was added to a lower layer, and it was then stirred and left at rest for 10 minutes. Thereafter, an upper layer was removed. A sodium hydroxide aqueous solution (prepared by dissolving 0.593 g of sodium hydroxide in 5.00 mL of water) was added to a lower layer. Subsequently, while keeping the internal temperature at 15 to 20° C., 2.68 mL (31.5 mmol) of 40.0% v/w hydrogen peroxide was added dropwise to the mixture. The obtained mixture was stirred at 25° C. for 30 minutes, and the pH of the solution was adjusted to pH 6.5 to 8.0 by hydrochloric acid. Thereafter, the mixture was heated to 40° C., so that the solid was completely dissolved in the solution. Thereafter, 0.250 g of activated carbon (SHIRASAGI A) was added to the reaction solution, and the obtained mixture was then stirred at 40° C. for 30 minutes, followed by filtration. A solid on a Nutsche was washed with 5.00 mL of water, and hydrochloric acid was then added to a mixed solution of a filtrate and a washing solution at an internal temperature of 35 to 45° C., so that the pH thereof was adjusted to pH 3 to 4. The mixed solution was cooled to 0 to 5° C., and it was then stirred for 1 hour. Thereafter, the precipitated solid was filtrated, and it was then washed with 5.00 mL of water and 5.00 mL of isopropyl alcohol, so as to obtain 2.06 g of a white solid (T-705). Yield: 84.0%.

INDUSTRIAL APPLICABILITY

The present invention is useful for production of T-705 that is useful for the treatment such as prevention and therapy of influenza virus infection, and the like.

The invention claimed is:
1. A compound represented by the following formula (I):

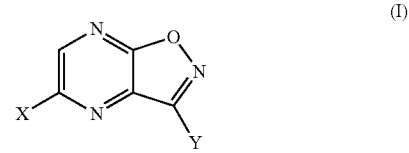

wherein X represents a halogen atom, a hydroxy group or a sulfamoyloxy group, wherein a nitrogen atom of the sulfamoyloxy group may be substituted with a hydroxy group, an amino group, an alkyl group, an aryl group, a heterocyclic group, or an alkylene group with or without the mediation of a heteroatom, and said substituent may further have one or more substituents which are selected from substituent group A; and Y represents —C(=O)R or —CN; wherein R represents a hydrogen atom, an alkoxy group, an aryloxy group, an alkyl group, an aryl group or an amino group;
wherein the alkoxy group, aryloxy group, alkyl group, and aryl group may be optionally substituted with one or more substituents selected from substituent group A, and the amino group may be optionally substituted with a substituent which is selected from a hydroxy group, an amino group, an alkyl group, an aryl group, a heterocyclic group or an alkylene group with or without the mediation of a heteroatom, and said substituent may further have one or more substituents which are selected from substituent group A; substituent group A: an alkyl group containing 1 to 10 carbon atoms, an alkenyl group containing 2 to 10 carbon atoms, an alkynyl group containing 2 to 10 carbon atoms, an alkoxy group containing 1 to 10 carbon atoms, an aryloxy group containing 6 to 10 carbon atoms, a halogen atom, an aryl group containing 6 to 10 carbon atoms, a hydroxy group, an amino group, an acylamino group containing 1 to 10 carbon atoms, an alkylsulfonylamino group containing 1 to 10 carbon atoms, a carbamoyl group containing 1 to 10 carbon atoms, a sulfamoyl group containing 0 to 10 carbon atoms, a carboxyl group, an alkoxycarbonyl group containing 2 to 10 carbon atoms, an acyloxy group containing 2 to 12 carbon atoms, a heterocyclic group, a cyano group, and a nitro group.

2. The compound according to claim 1, wherein Y represents —C(═O)R where R represents an alkoxy group or an amino group, wherein the alkoxy group may be optionally substituted with one or more substituents selected from the substituent group A, and the amino group may be optionally substituted with a substituent which is selected from a hydroxy group, an amino group, an alkyl group, an aryl group, a heterocyclic group or an alkylene group with or without the mediation of a heteroatom, and said substituent may further have one or more substituents which are selected from the substituent group A.

3. The compound according to claim 2, wherein X represents a hydroxy group, a chlorine atom or a fluorine atom.

4. The compound according to claim 1, wherein X represents a hydroxy group, a chlorine atom or a fluorine atom.

5. The compound according to claim 1, wherein X represents a fluorine atom or a chlorine atom, and Y represents —C(═O)R where R represents an alkoxy group which may be optionally substituted with one or more substituents selected from the substituent group A.

6. The compound according to claim 1, wherein X represents a fluorine atom or a chlorine atom, and Y represents —C(═O)R where R represents a methoxy group, an ethoxy group, an n-propoxy group, an isopropoxy group, or an n-butoxy group.

7. A method for producing a compound represented by the following formula (I-1):

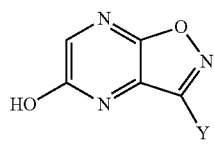

(I-1)

which comprises treating a compound represented by the following formula (II):

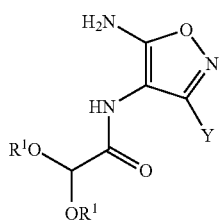

(II)

with an acid;
wherein, in formula (I-1) and formula (II),
Y represents —C(═O)R or —CN;
R represents a hydrogen atom, an alkoxy group, an aryloxy group, an alkyl group, an aryl group or an amino group; wherein said alkoxy group, aryloxy group, alkyl group, and aryl group may be optionally substituted with one or more substituents selected from substituent group A, and said amino group may be optionally substituted with a substituent which is selected from a hydroxy group, an amino group, an alkyl group, an aryl group, a heterocyclic group or an alkylene group with or without the mediation of a heteroatom, and said substituent may further have one or more substituents which are selected from substituent group A; and in formula (II),
$R^1$ represents a hydrogen atom or an alkyl group; wherein said alkyl group may be optionally substituted with one or more substituents selected from the substituent group A,
substituent group A: an alkyl group containing 1 to 10 carbon atoms, an alkenyl group containing 2 to 10 carbon atoms, an alkynyl group containing 2 to 10 carbon atoms, an alkoxy group containing 1 to 10 carbon atoms, an aryloxy group containing 6 to 10 carbon atoms, a halogen atom, an aryl group containing 6 to 10 carbon atoms, a hydroxy group, an amino group, an acylamino group containing 1 to 10 carbon atoms, an alkylsulfonylamino group containing 1 to 10 carbon atoms, a carbamoyl group containing 1 to 10 carbon atoms, a sulfamoyl group containing 0 to 10 carbon atoms, a carboxyl group, an alkoxycarbonyl group containing 2 to 10 carbon atoms, an acyloxy group containing 2 to 12 carbon atoms, a heterocyclic group, a cyano group and a nitro group.

8. A method for producing a compound represented by the following formula (J-4):

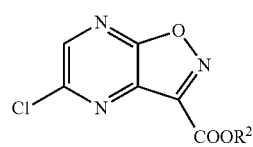

(J-4)

which comprises reacting a compound represented by the following formula (J-3):

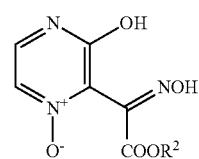

(J-3)

with a chlorinating agent selected from phosphorous oxychloride, thionyl chloride, phosphorus pentachloride, phosphorus trichloride, pyrocatechyl phosphotrichloride, dichlorotriphenylphosphorane and oxalyl chloride, or a combination thereof;
wherein, in formula (J-3) and formula (J-4),
$R^2$ represents an alkyl group or an aryl group; wherein said alkyl group and aryl group may be optionally substituted with one or more substituents selected from substituent group A;
substituent group A: an aryl group containing 1 to 10 carbon atoms, an alkenyl group containing 2 to 10 carbon atoms, an alkynyl group containing 2 to 10 carbon atoms, an alkoxy group containing 1 to 10 carbon atoms, an aryloxy group containing 6 to 10 carbon atoms, a halogen atom, an aryl group containing 6 to 10 carbon atoms, a hydroxy group, an amino group, an acylamino group containing 1 to 10 carbon atoms, an alkylsulfonylamino group containing 1 to 10 carbon atoms, a carbamoyl group containing 1 to 10 carbon atoms, a sulfamoyl group containing 0 to 10 carbon atoms, a carboxyl group, an alkoxycarbonyl group containing 2 to 10 carbon atoms, an acyloxy group containing 2 to 12 carbon atoms, a heterocyclic group, and a nitro group.

9. A method for producing a compound represented by the following formula (J-5):

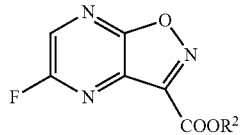
(J-5)

which comprises reacting a compound represented by the following formula (J-4):

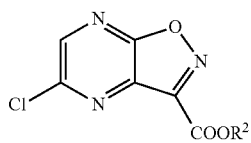
(J-4)

with a fluorinating agent selected from the group consisting of potassium fluoride, cesium fluoride, tetra-n-butylammonium fluoride, tetramethylammonium fluoride, tetraphenylphosphonium fluoride or a combination thereof, in the presence of 2,4-dinitrochlorobenzene or 2,4-dinitrofluorobenzene, where, in formula (J-4) and formula (J-5), $R^2$ represents an alkyl group or an aryl group; wherein said alkyl group and aryl group may be optionally substituted with one or more substituents selected from substituent group A;

substituent group A: an alkyl group containing 1 to 10 carbon atoms, an alkenyl group containing 2 to 10 carbon atoms, an alkynyl group containing 2 to 10 carbon atoms, an alkoxy group containing 1 to 10 carbon atoms, an aryloxy group containing 6 to 10 carbon atoms, a halogen atom, an aryl group containing 6 to 10 carbon atoms, a hydroxy group, an amino group, an acylamino group containing 1 to 10 carbon atoms, an alkylsulfonylamino group containing 1 to 10 carbon atoms, a carbamoyl group containing 1 to 10 carbon atoms, a sulfamoyl group containing 0 to 10 carbon atoms, a carboxyl group, an alkoxycarbonyl group containing 2 to 10 carbon atoms, an acyloxy group containing 2 to 12 carbon atoms, a heterocyclic group, a cyano group, and a nitro group.

* * * * *